United States Patent
Hasegawa et al.

(10) Patent No.: US 12,383,664 B2
(45) Date of Patent: Aug. 12, 2025

(54) BLOOD PURIFICATION APPARATUS AND METHOD OF ACQUIRING PLASMA FLOW RATE ON BLOOD PURIFICATION APPARATUS

(71) Applicant: Nikkiso Company Limited, Tokyo (JP)

(72) Inventors: Shinya Hasegawa, Shizuoka (JP); Satoru Kawarabayashi, Tokyo (JP); Masahiro Toyoda, Shizuoka (JP); Kunihiko Akita, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 1044 days.

(21) Appl. No.: 17/104,621

(22) Filed: Nov. 25, 2020

(65) Prior Publication Data

US 2021/0077703 A1 Mar. 18, 2021

Related U.S. Application Data

(63) Continuation of application No. PCT/JP2019/024333, filed on Jun. 19, 2019.

(30) Foreign Application Priority Data

Jun. 20, 2018 (JP) ................. 2018-116786

(51) Int. Cl.
*A61M 1/36* (2006.01)
*A61M 1/34* (2006.01)

(52) U.S. Cl.
CPC ........ *A61M 1/3601* (2014.02); *A61M 1/3413* (2013.01); *A61M 2230/207* (2013.01)

(58) Field of Classification Search
None
See application file for complete search history.

(56) References Cited

U.S. PATENT DOCUMENTS

| 4,640,445 A | 2/1987 | Yamada |
| 6,406,631 B1 | 6/2002 | Collins et al. |
(Continued)

FOREIGN PATENT DOCUMENTS

| JP | H06-218047 A | 8/1994 |
| JP | H07-265416 A | 10/1995 |
(Continued)

OTHER PUBLICATIONS

Khazaei et al., "A new equation for calculation of colloid osmotic pressure based on serum total protein concentration and UV-light absorption", Current Anaesthesia and Critical Care, vol. 19, Issue 1, 2008, pp. 8-11, 4 total pages (Year: 2008).*

(Continued)

*Primary Examiner* — Jonathan M Peo
(74) *Attorney, Agent, or Firm* — Young Basile Hanlon & MacFarlane, P.C.

(57) ABSTRACT

A blood purification apparatus includes a blood circuit that allows a patient's blood to extracorporeally circulate; a blood purifier between the arterial blood circuit and the venous blood circuit having a blood flow route through which the blood extracorporeally flows and a dialysate flow route through which dialysate flows, the blood flow route and the dialysate flow route being separated from each other by a blood purification membrane; an ultrafiltration unit that filters out water from the blood in the blood flow route through the blood purification membrane and drains the water through the dialysate flow route; and a substitution-fluid supply unit that supplies substitution fluid. The blood purification apparatus includes a plasma-flow-rate-acquiring unit that acquires a plasma flow rate or a correlation value of plasma flow rate with reference to a blood concentration detected from the patient's blood and a plasma total protein detected from the blood.

16 Claims, 11 Drawing Sheets

(56) References Cited

U.S. PATENT DOCUMENTS

| | | |
|---|---|---|
| 7,758,532 B2 | 7/2010 | Mori et al. |
| 8,795,218 B2 | 8/2014 | Lannoy |
| 2004/0068219 A1 | 4/2004 | Summerton et al. |
| 2009/0221948 A1* | 9/2009 | Szamosfalvi ....... A61M 1/3441 604/6.07 |
| 2010/0168639 A1 | 7/2010 | Cantu et al. |
| 2012/0265117 A1* | 10/2012 | Fava ................... A61M 1/3621 604/6.09 |
| 2014/0305869 A1 | 10/2014 | Wolff et al. |

FOREIGN PATENT DOCUMENTS

| | | |
|---|---|---|
| JP | 2002-126075 A | 5/2002 |
| JP | 2011-110098 A | 6/2011 |
| JP | 2011-200407 A | 10/2011 |
| JP | 2013-027455 A | 2/2013 |
| WO | 2001/076661 A1 | 10/2001 |
| WO | 2012/042323 A2 | 4/2012 |
| WO | 2018/017623 A1 | 1/2018 |

OTHER PUBLICATIONS

International Search Report dated Sep. 10, 2019 for Application No. PCT/JP2019/024333 published as WO2019244941.
Potentially related U.S. Appl. No. 17/104,626, filed Nov. 25, 2020 entitled "Blood Purification Apparatus and Method of Estimating Patient's State of Nutrition On Blood Purification Apparatus," Published as WO2019244942.
European Search Report for Application No. 19822015.4, dated Mar. 21, 2022.
Chinese First Office Action for Application No. 201980040897.1, dated Jan. 31, 2023, with English translation, 19 pgs.
Chinese Second Office Action for Application No. 201980040897.1, dated Sep. 28, 2023, with English translation, 25 pgs.

* cited by examiner

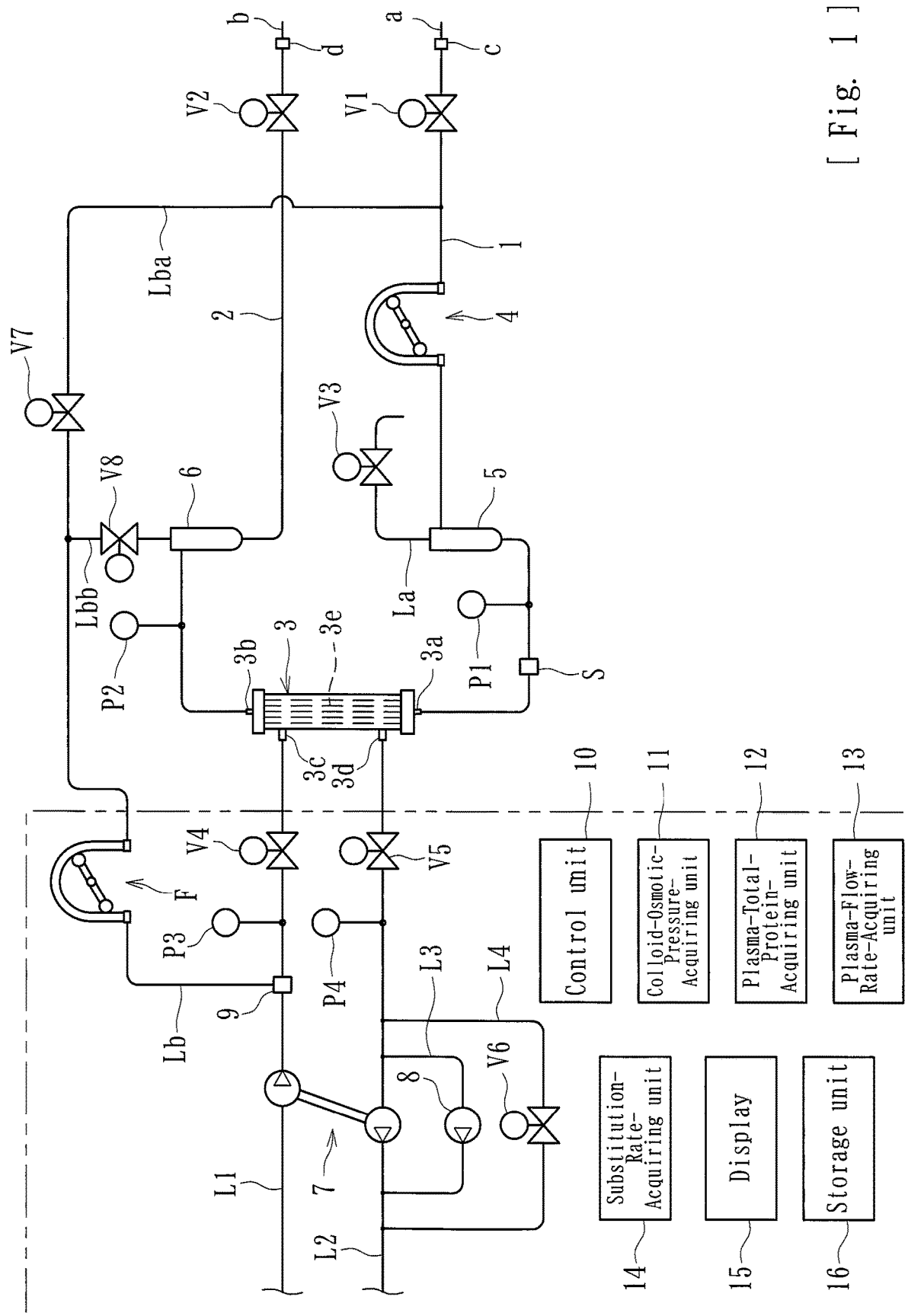
[Fig. 1]

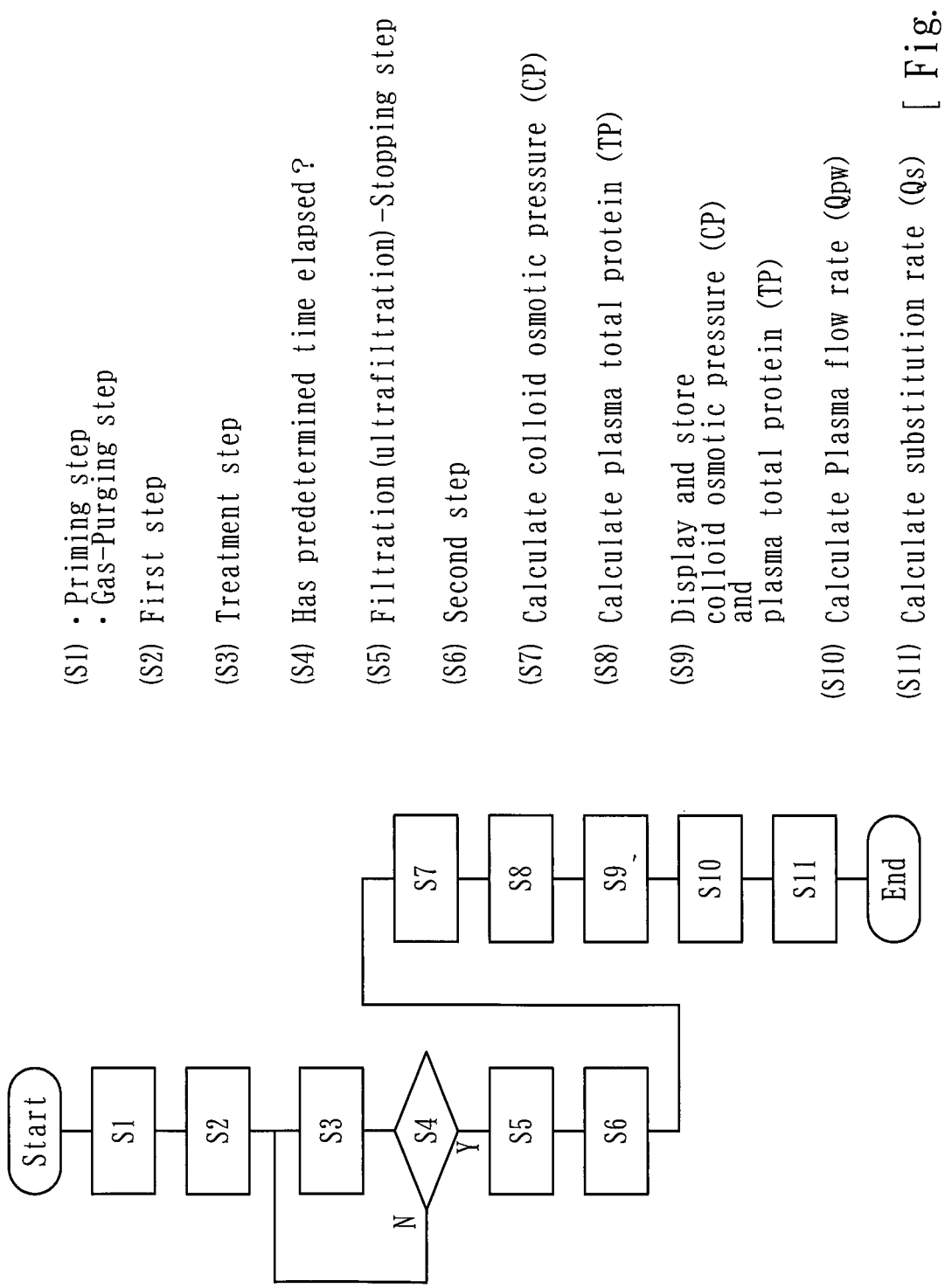

[Fig. 2]

(S1) · Priming step
· Gas-Purging step
(S2) First step
(S3) Treatment step
(S4) Has predetermined time elapsed ?
(S5) Filtration(ultrafiltration)-Stopping step
(S6) Second step
(S7) Calculate colloid osmotic pressure (CP)
(S8) Calculate plasma total protein (TP)
(S9) Display and store
colloid osmotic pressure (CP)
and
plasma total protein (TP)
(S10) Calculate Plasma flow rate (Qpw)
(S11) Calculate substitution rate (Qs)

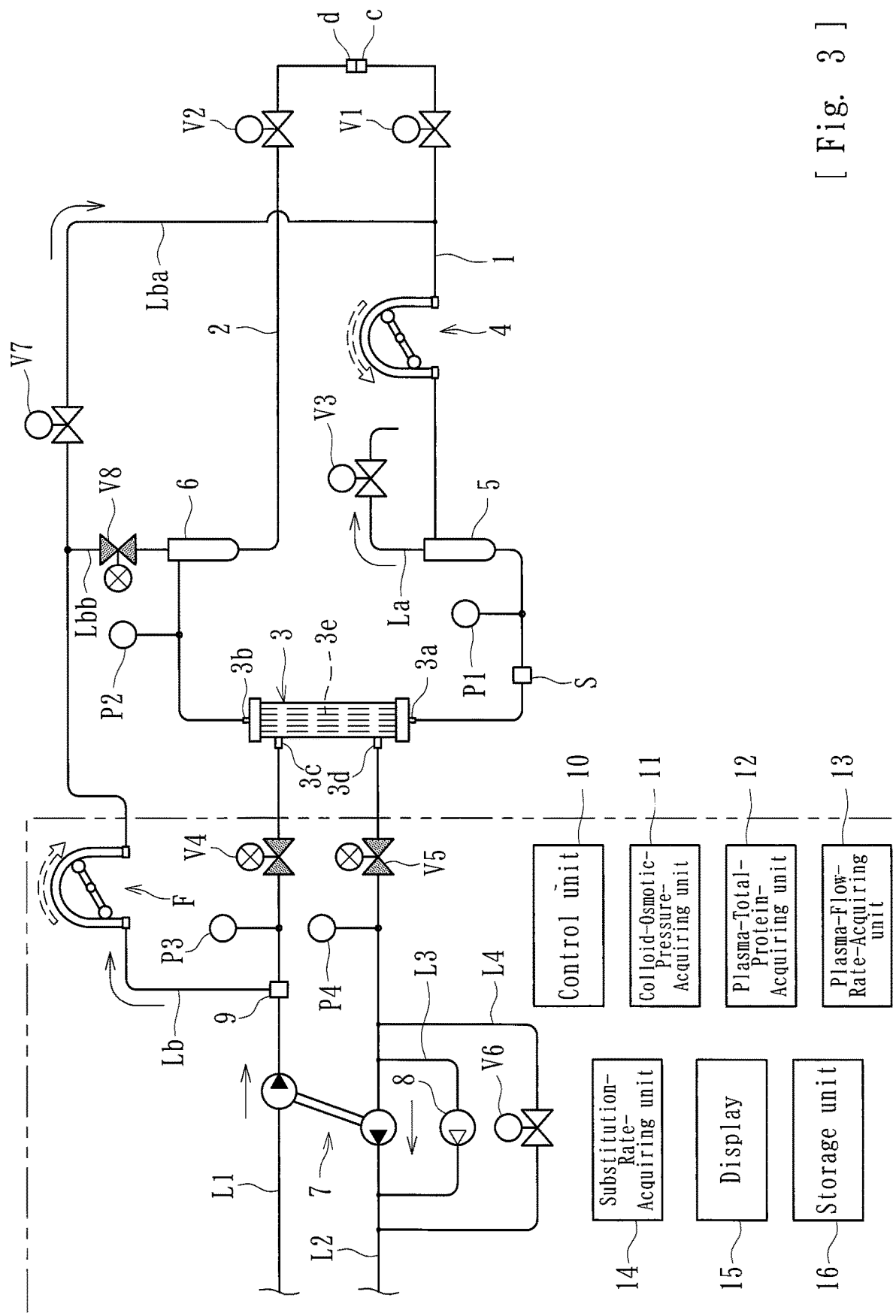
[Fig. 3]

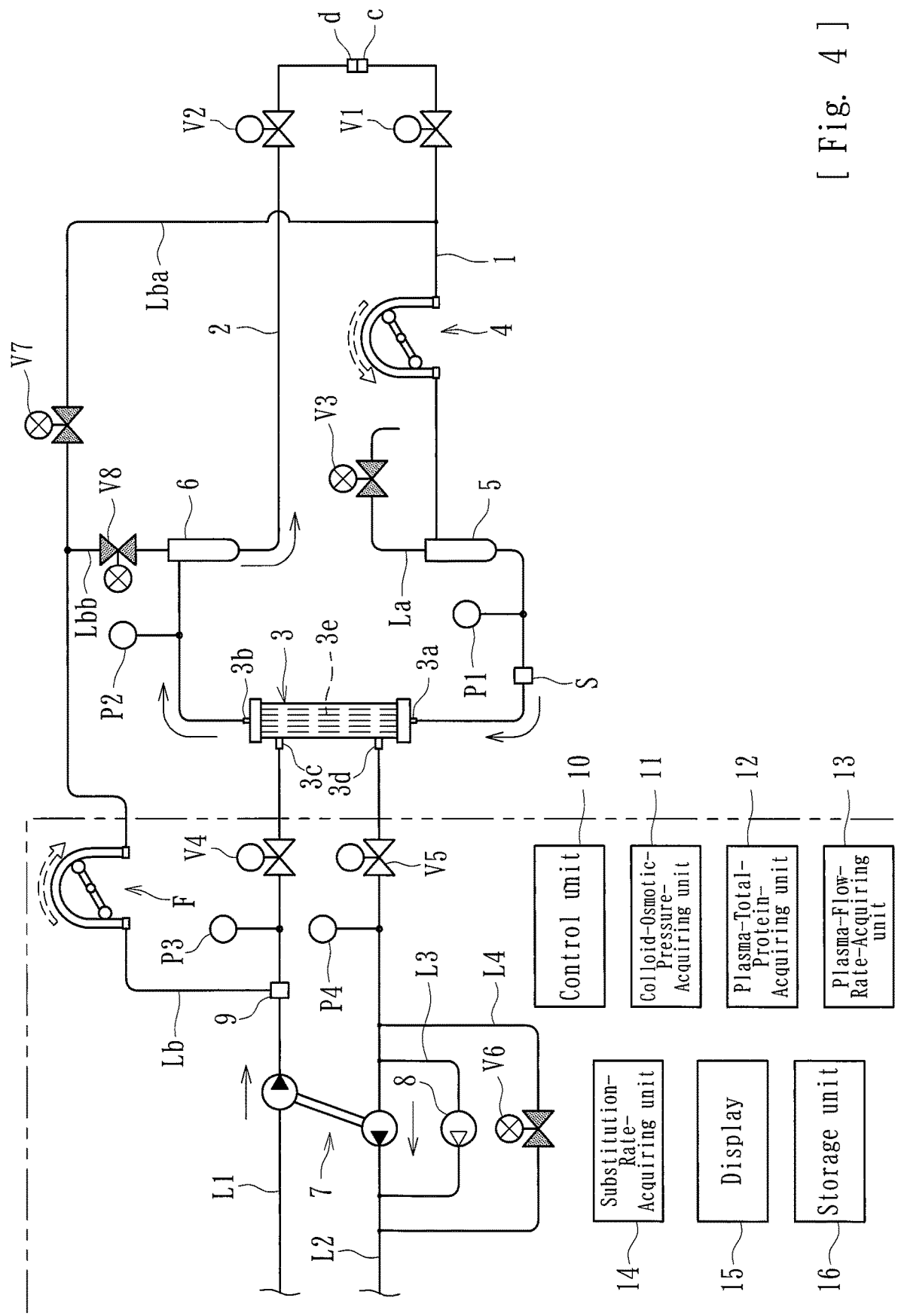
[Fig. 4]

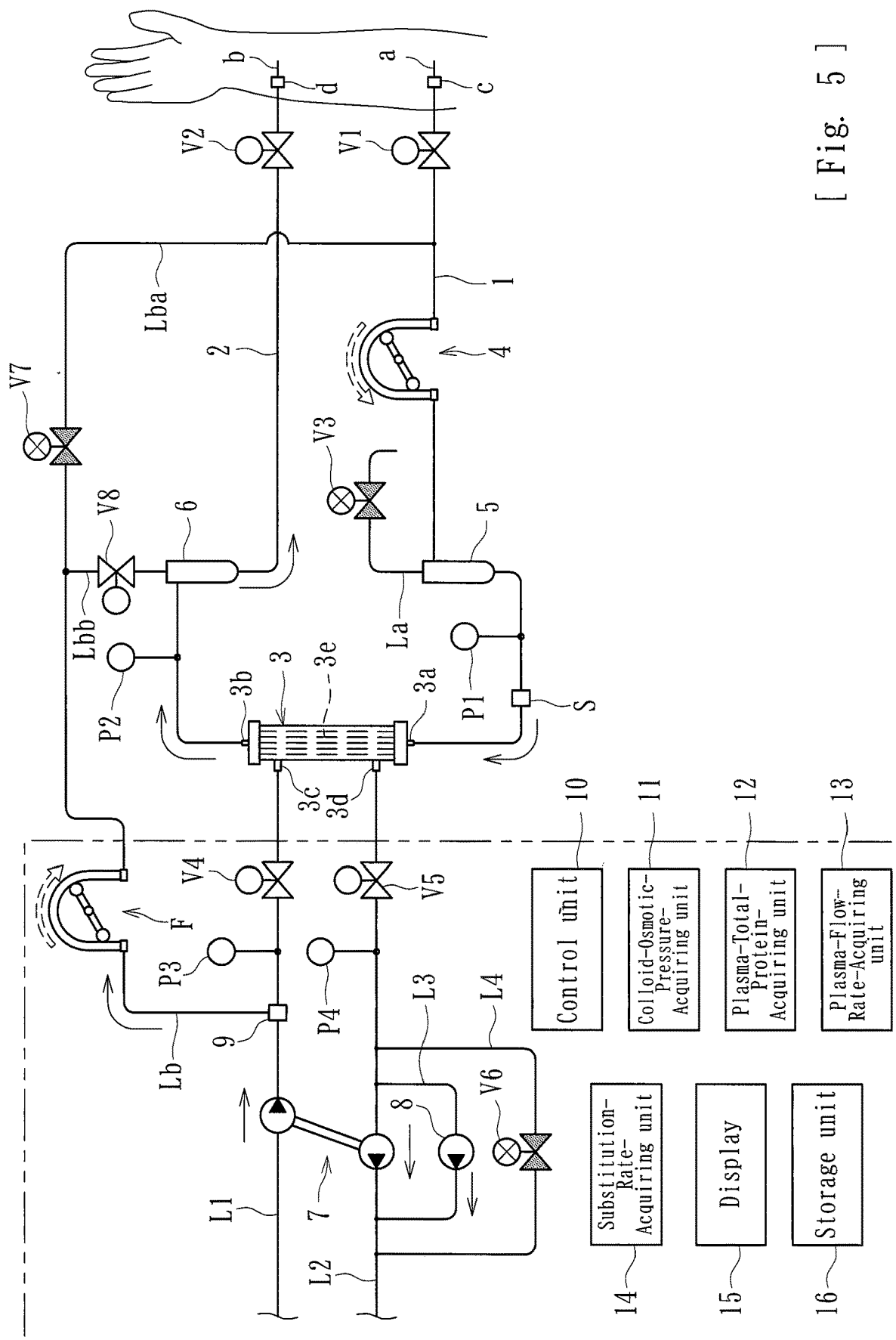
[Fig. 5]

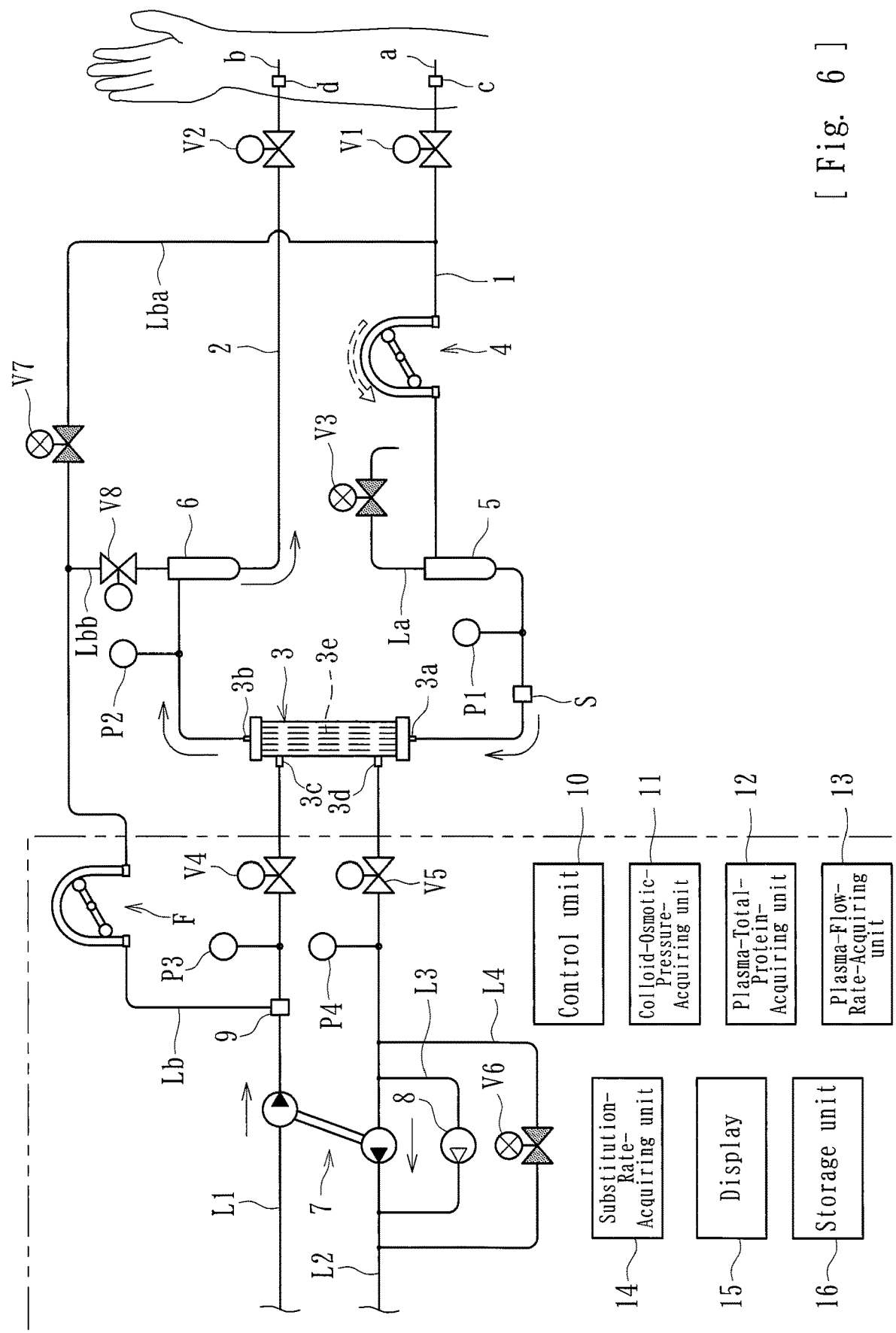
[ Fig. 6 ]

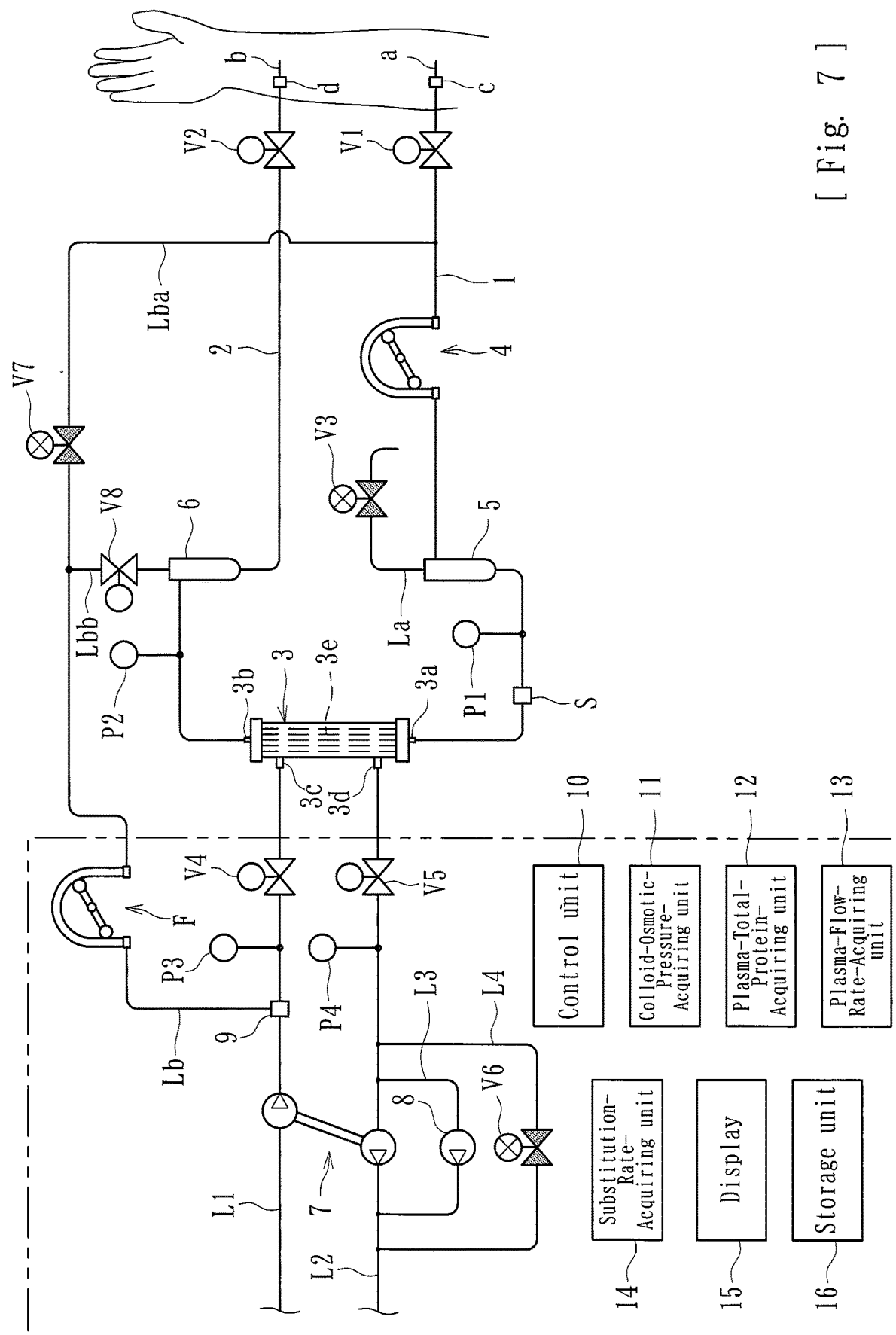
[Fig. 7]

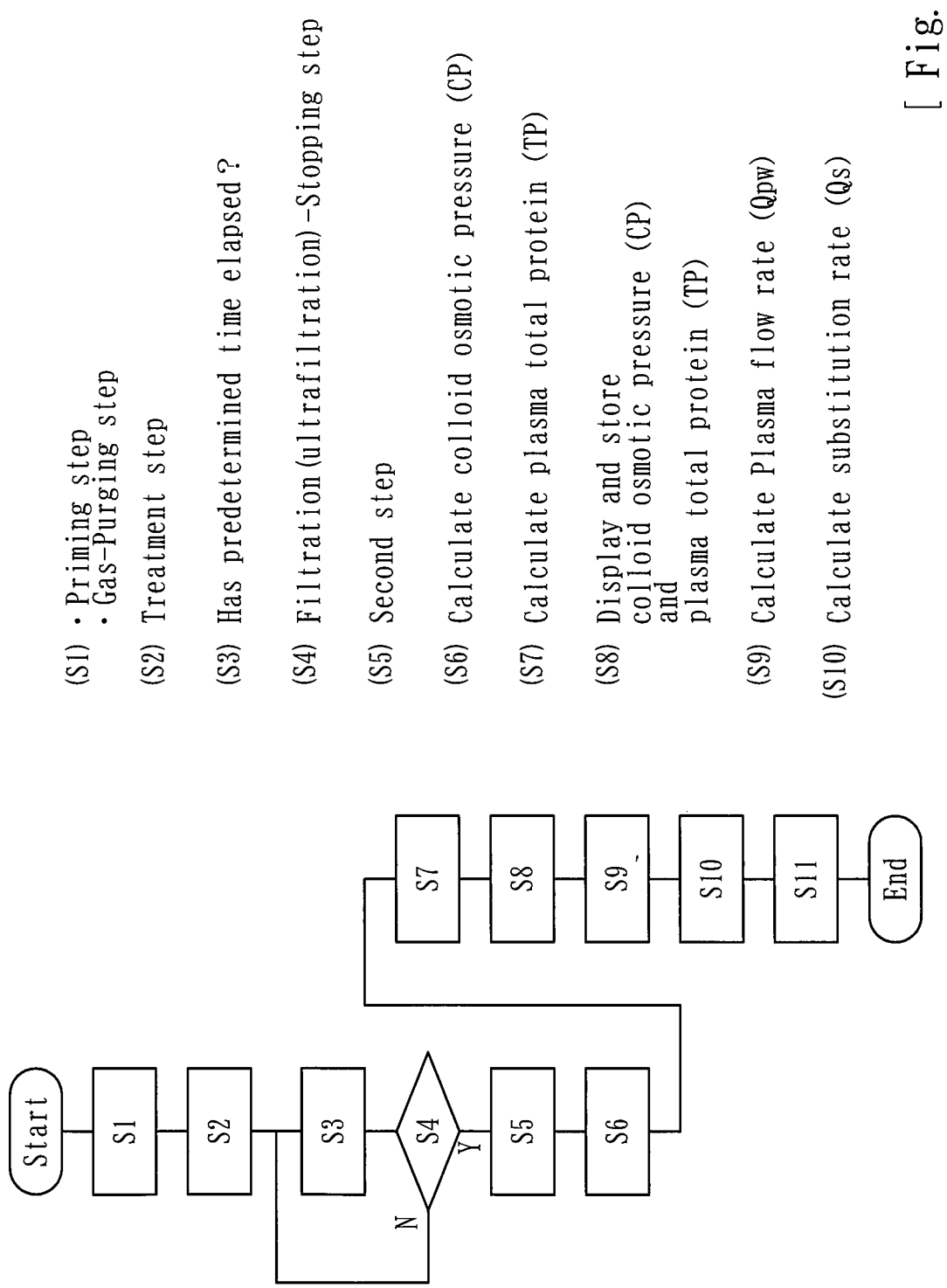

[Fig. 8]

(S1) • Priming step
• Gas-Purging step
(S2) Treatment step
(S3) Has predetermined time elapsed ?
(S4) Filtration(ultrafiltration)-Stopping step
(S5) Second step
(S6) Calculate colloid osmotic pressure (CP)
(S7) Calculate plasma total protein (TP)
(S8) Display and store
colloid osmotic pressure (CP)
and
plasma total protein (TP)
(S9) Calculate Plasma flow rate (Qpw)
(S10) Calculate substitution rate (Qs)

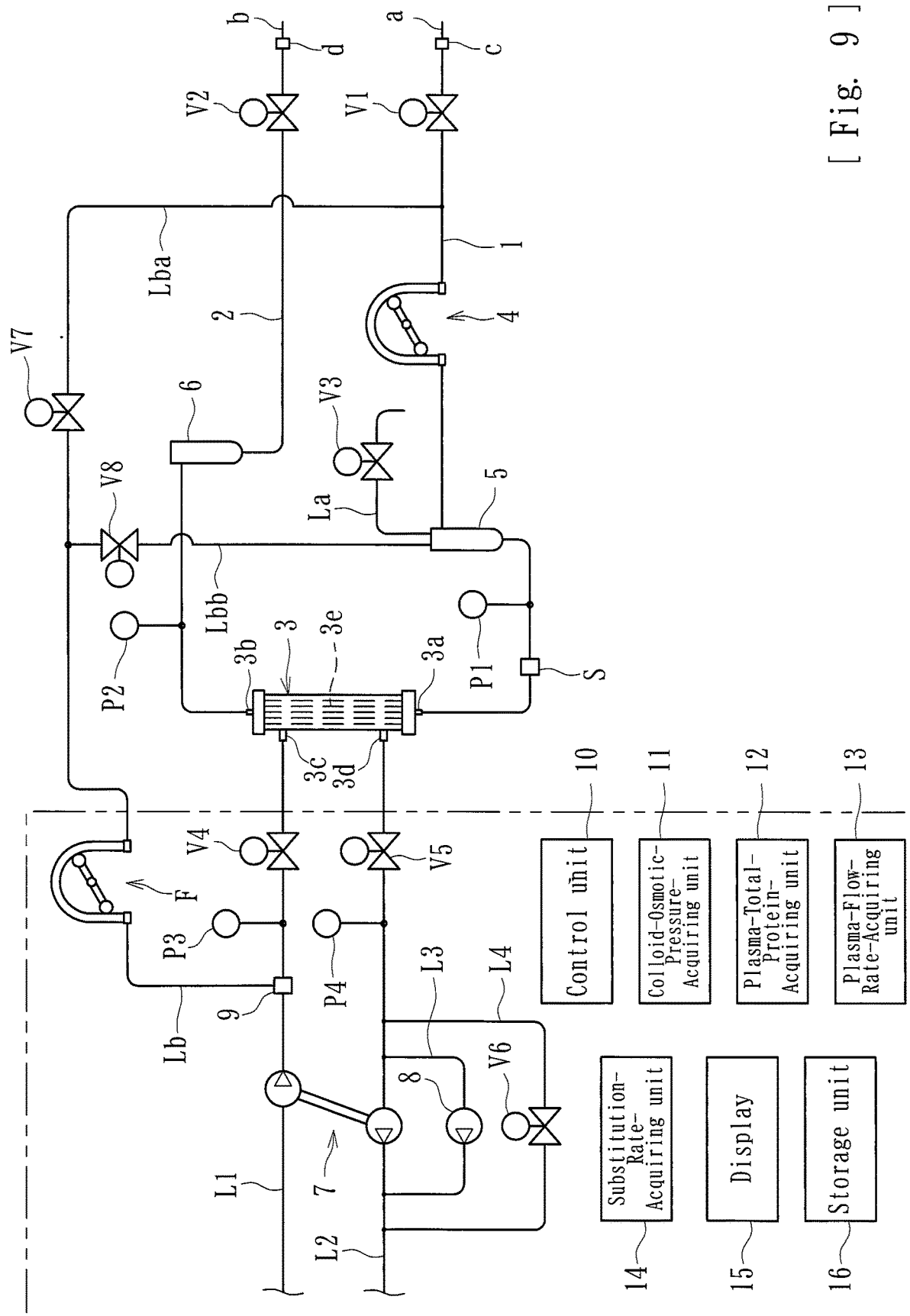
[Fig. 9]

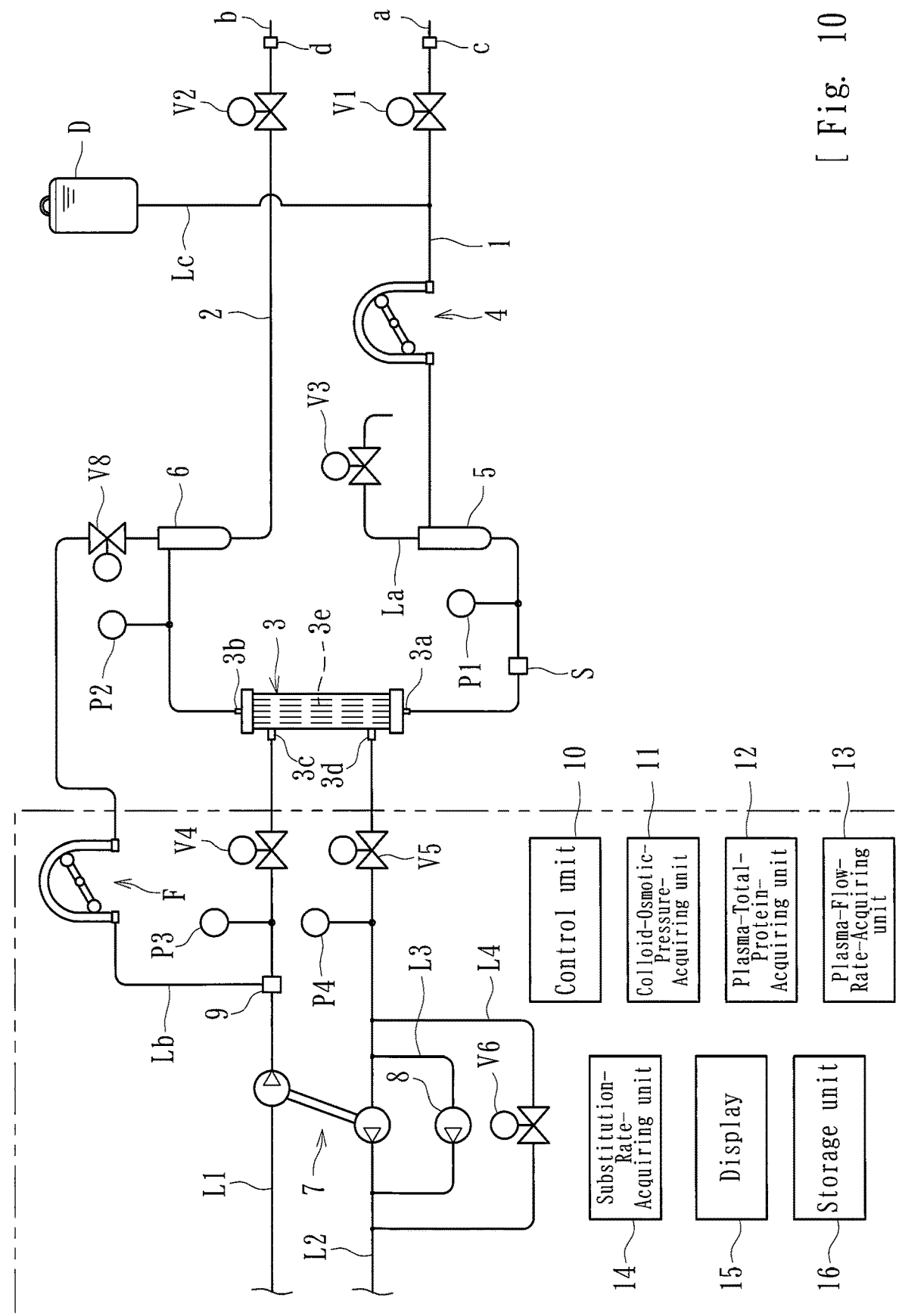
[Fig. 10]

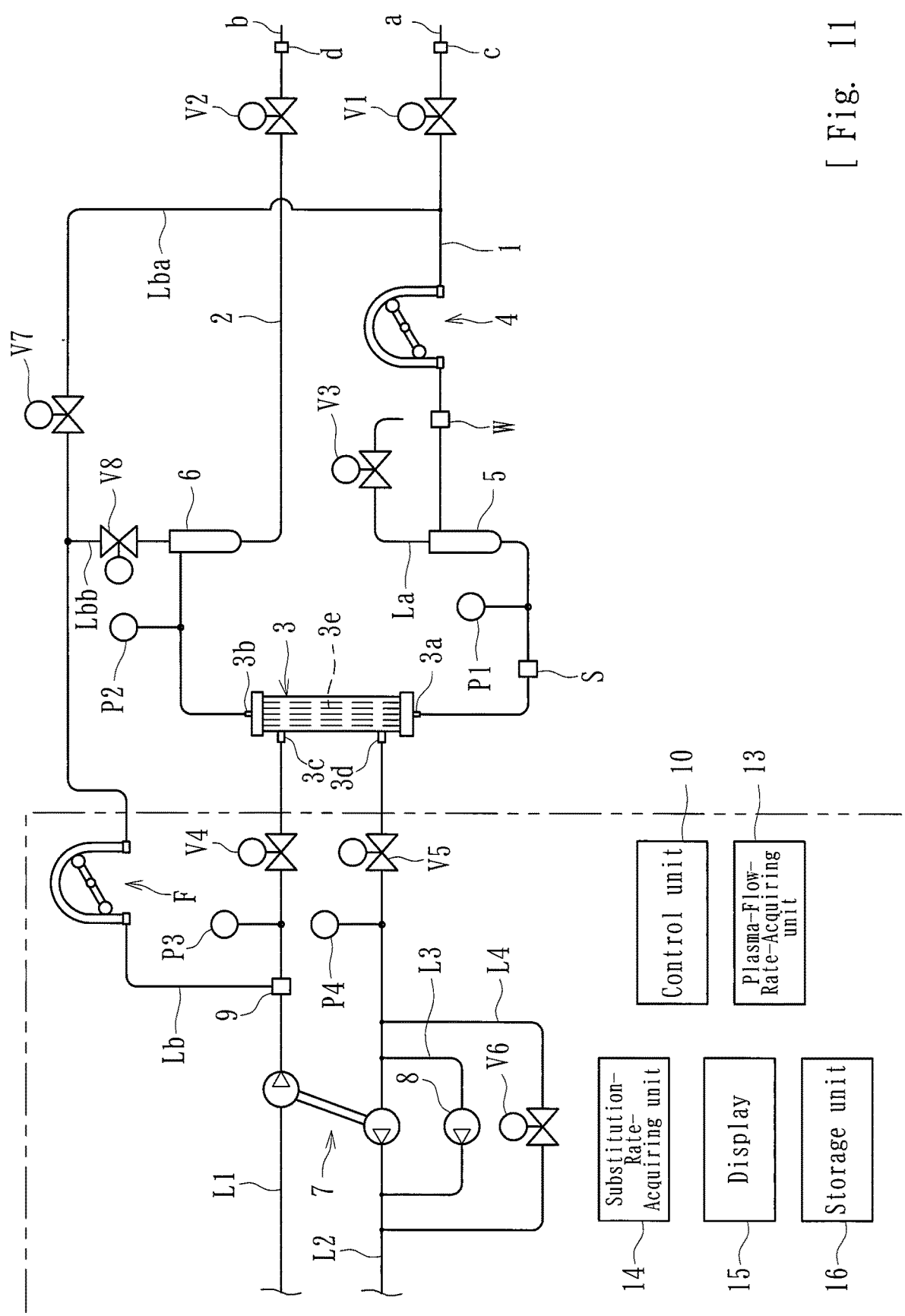
[Fig. 11]

BLOOD PURIFICATION APPARATUS AND METHOD OF ACQUIRING PLASMA FLOW RATE ON BLOOD PURIFICATION APPARATUS

CROSS-REFERENCE TO RELATED APPLICATION(S)

This application is a continuation of International Application No. PCT/JP2019/024333, published as WO2019/244941, filed on Jun. 19, 2019, which claims priority to Japanese Application No. 2018-116786, filed on Jun. 20, 2018, the entire disclosures of which are hereby incorporated by reference.

FIELD

The present invention relates to a blood purification apparatus for purifying a patient's blood while causing the blood to extracorporeally circulate in dialysis treatment or the like performed with a dialyzer, and also relates to a method of acquiring a plasma flow rate on a blood purification apparatus.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

In particular, the arterial blood circuit includes a squeezable tube and is provided with a peristaltic blood pump. The blood pump is capable of delivering liquid by squeezing the squeezable tube with rollers. When the blood pump is activated, the patient's blood can be caused to extracorporeally circulate through the blood circuit. Thus, the blood in extracorporeal circulation undergoes blood purification treatment in the dialyzer (see PTL 1, for example).

PTL 1: Japanese Unexamined Patent Application Publication No. 2011-110098 the teachings of which are expressly incorporated by reference herein for all purposes.

SUMMARY

The above known blood purification apparatus has the following problem.

According to recent reports on some treatments (such as HDF and HF) accompanied by substitution, the greater the substitution volume, the better the life prognosis. Hence, there has been a growing demand for increasing the substitution rate as high as possible during the treatment. The substitution rate is determined by the plasma flow rate at which plasma is filterable from blood. However, since blood contains blood cells and proteins, the volume of plasma that can be filtered out is limited.

The plasma flow rate (Qpw) at which plasma is filterable is known as the following mathematical expression:

$$Qpw = Qb \times (1-Ht) \times (1-0.0107 \times TP)$$

where Qb denotes blood flow rate (mL/min), Ht denotes hematocrit (%), and TP denotes plasma total protein (g/dL).

The optimum substitution rate for achieving a certain filtration fraction is considered to be determined by calculating the plasma flow rate at which plasma is filterable through the above expression. However, the hematocrit (Ht) and the plasma total protein (TP) need to be obtained in advance through a blood test or the like and to be inputted as patient data to the blood purification apparatus at the time of blood purification treatment. In particular, the value of plasma total protein (TP) changes with the state of nutrition and may be significantly different from the one obtained through the blood test. Such a situation makes it difficult to accurately calculate the plasma flow rate (Qpw).

The present invention has been conceived in view of the above circumstances and provides a blood purification apparatus capable of accurately calculating the plasma flow rate or the correlation value of plasma flow rate by detecting the plasma total protein from blood flowing through a blood circuit during blood purification treatment, and also provides a method of acquiring the plasma flow rate on a blood purification apparatus.

Variation 1 may include a blood purification apparatus that includes a blood circuit including an arterial blood circuit and a venous blood circuit and that allows a patient's blood to extracorporeally circulate from a distal end of the arterial blood circuit to a distal end of the venous blood circuit; a blood purifier provided between the arterial blood circuit and the venous blood circuit and that purifies the blood flowing through the blood circuit, the blood purifier having a blood flow route through which the blood extracorporeally circulating through the blood circuit flows and a dialysate flow route through which dialysate flows, the blood flow route and the dialysate flow route being separated from each other by a blood purification membrane for purifying the blood; an ultrafiltration unit that performs ultrafiltration by filtering out water from the blood in the blood flow route through the blood purification membrane and draining the water through the dialysate flow route; and a substitution-fluid supply unit that supplies substitution fluid into the blood circuit. The blood purification apparatus includes a plasma-flow-rate-acquiring unit that acquires a plasma flow rate or a correlation value of plasma flow rate with reference to a blood concentration detected from the patient's blood and a plasma total protein detected from the blood flowing through the blood circuit.

Variation 2 may include the blood purification apparatus according to variation 1 and may comprise a substitution rate to be achieved by the substitution-fluid supply unit is calculated with reference to the plasma flow rate or the correlation value of plasma flow rate acquired by the plasma-flow-rate-acquiring unit.

Variation 3 may include the blood purification apparatus according to variation 1 or 2 and may further include a detecting unit that detects a transmembrane pressure difference occurring on the blood purification membrane under a pressure difference between liquid in the blood flow route and liquid in the dialysate flow route; a colloid-osmotic-pressure-acquiring unit that acquires a colloid osmotic pressure of the blood in the blood flow route or a correlation value of colloid osmotic pressure with reference to the transmembrane pressure difference occurring when liquid that does not generate colloid osmotic pressure is supplied into the blood flow route with the filtration by the ultrafiltration unit withheld and the transmembrane pressure difference occurring when the patient's blood is supplied into the blood flow route with the filtration by the ultrafiltration unit withheld; and a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit. Furthermore, the plasma-flow-rate-acquiring unit acquires the plasma flow rate or the correlation value of plasma flow rate with reference to the blood concentration detected from the patient's blood and the plasma total protein or the correlation value of plasma total protein acquired by the plasma-total-protein-acquiring unit.

Variation 4 may comprise the blood purification apparatus according to variation 3 and may further include a control unit that executes a first step in which the liquid that does not generate colloid osmotic pressure is supplied into the blood flow route with the filtration by the ultrafiltration unit withheld, and the transmembrane pressure difference is calculated by using the detecting unit; and a second step in which the patient's blood is supplied into the blood flow route with the filtration by the ultrafiltration unit withheld, and the transmembrane pressure difference is calculated by using the detecting unit. Furthermore, the colloid-osmotic-pressure-acquiring unit acquires the colloid osmotic pressure or the correlation value of colloid osmotic pressure with reference to the transmembrane pressure difference calculated in the first step and the transmembrane pressure difference calculated in the second step.

Variation 5 may comprise the blood purification apparatus according to variation 4 and wherein the control unit is capable of sequentially executing a priming step in which a priming solution is supplied into the blood circuit and a treatment step in which blood purification treatment is performed with the blood purifier while the patient's blood is caused to extracorporeally circulate through the blood circuit. Furthermore, the liquid that does not generate colloid osmotic pressure and is supplied into the blood flow route in the first step is the priming solution that is used in the priming step, and the blood that is supplied into the blood flow route in the second step is the blood that is caused to extracorporeally circulate in the treatment step.

Variation 6 may comprise the blood purification apparatus according to variation 4 or 5 and wherein the control unit executes the first step and the second step while a flow of the liquid is stopped in the blood flow route and in the dialysate flow route.

Variation 7 may comprise the blood purification apparatus according to any of variations 1 to 6 and may further include a blood-concentration-detecting unit provided to the blood circuit and that detects the concentration of the blood flowing through the blood circuit on a time-course basis. Furthermore, the plasma-flow-rate-acquiring unit acquires the plasma flow rate or the correlation value of plasma flow rate with reference to the blood concentration detected on a time-course basis by the blood-concentration-detecting unit.

Variation 8 may provide a method of acquiring a plasma flow rate on a blood purification apparatus that includes a blood circuit including an arterial blood circuit and a venous blood circuit and that allows a patient's blood to extracorporeally circulate from a distal end of the arterial blood circuit to a distal end of the venous blood circuit; a blood purifier provided between the arterial blood circuit and the venous blood circuit and that purifies the blood flowing through the blood circuit, the blood purifier having a blood flow route through which the blood extracorporeally circulating through the blood circuit flows and a dialysate flow route through which dialysate flows, the blood flow route and the dialysate flow route being separated from each other by a blood purification membrane for purifying the blood; an ultrafiltration unit that performs ultrafiltration by filtering out water from the blood in the blood flow route through the blood purification membrane and draining the water through the dialysate flow route; and a substitution-fluid supply unit that supplies substitution fluid into the blood circuit. In the method, a plasma flow rate or a correlation value of plasma flow rate is acquired with reference to a blood concentration detected from the patient's blood and a plasma total protein detected from the blood flowing through the blood circuit.

Variation 9 may comprise the method of acquiring a plasma flow rate on a blood purification apparatus according to variation 8, a substitution rate to be achieved by the substitution-fluid supply unit is calculated with reference to the plasma flow rate or the correlation value of plasma flow rate.

Variation 10 may comprise to method of acquiring a plasma flow rate on a blood purification apparatus according to variation 8 or 9, wherein the blood purification apparatus further includes a detecting unit that detects a transmembrane pressure difference occurring on the blood purification membrane under a pressure difference between liquid in the blood flow route and liquid in the dialysate flow route; a colloid-osmotic-pressure-acquiring unit that acquires a colloid osmotic pressure of the blood in the blood flow route or a correlation value of colloid osmotic pressure with reference to the transmembrane pressure difference occurring when liquid that does not generate colloid osmotic pressure is supplied into the blood flow route with the filtration by the ultrafiltration unit withheld and the transmembrane pressure difference occurring when the patient's blood is supplied into the blood flow route with the filtration by the ultrafiltration unit withheld; and a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit. Furthermore, the plasma flow rate or the correlation value of plasma flow rate is acquired with reference to the blood concentration detected from the patient's blood and the plasma total protein or the correlation value of plasma total protein acquired by the plasma-total-protein-acquiring unit.

Variation 11 may comprise the method of acquiring a plasma flow rate on a blood purification apparatus according to variation 10, wherein the blood purification apparatus further includes a control unit that executes a first step in which the liquid that does not generate colloid osmotic pressure is supplied into the blood flow route with the filtration by the ultrafiltration unit withheld, and the transmembrane pressure difference is calculated by using the detecting unit; and a second step in which the patient's blood is supplied into the blood flow route with the filtration by the ultrafiltration unit withheld, and the transmembrane pressure difference is calculated by using the detecting unit. Furthermore, the colloid osmotic pressure or the correlation value of colloid osmotic pressure is acquired with reference to the transmembrane pressure difference calculated in the first step and the transmembrane pressure difference calculated in the second step.

Variation 12 may comprise the method of acquiring a plasma flow rate on a blood purification apparatus according to variation 11 and may comprise the control unit sequentially executes a priming step in which a priming solution is supplied into the blood circuit and a treatment step in which blood purification treatment is performed with the blood purifier while the patient's blood is caused to extracorporeally circulate through the blood circuit. Furthermore, the liquid that does not generate colloid osmotic pressure and is supplied into the blood flow route in the first step is the priming solution that is used in the priming step, and the blood that is supplied into the blood flow route in the second step is the blood that is caused to extracorporeally circulate in the treatment step.

Variation 13 may comprise the method of acquiring a plasma flow rate on a blood purification apparatus according to variation 11 or 12, wherein the control unit executes the first step and the second step while a flow of the liquid is stopped in the blood flow route and in the dialysate flow route.

Variation 14 may comprise the method of acquiring a plasma flow rate on a blood purification apparatus according to any of variations 8 to 13, the blood purification apparatus further includes a blood-concentration-detecting unit provided to the blood circuit and that is capable of detecting the concentration of the blood flowing through the blood circuit on a time-course basis. Furthermore, the plasma flow rate or the correlation value of plasma flow rate is acquired with reference to the blood concentration detected on a time-course basis by the blood-concentration-detecting unit.

Variations 1 and 8 may comprise the plasma flow rate or the correlation value of plasma flow rate is acquired with reference to the blood concentration detected from the patient's blood and the plasma total protein detected from the blood flowing through the blood circuit. Therefore, the plasma flow rate or the correlation value of plasma flow rate can be calculated accurately by detecting the plasma total protein from the blood flowing through the blood circuit during the blood purification treatment.

Variations 2 and 9 may comprise the substitution rate to be achieved by the substitution-fluid supply unit is calculated with reference to the plasma flow rate or the correlation value of plasma flow rate. Therefore, substitution can be achieved at a substitution rate that is optimum for the plasma flow rate or the correlation value of plasma flow rate.

Variations 3 and 10 may comprise the blood purification apparatus further includes the detecting unit, the colloid-osmotic-pressure-acquiring unit, and the plasma-total-protein-acquiring unit, so that the plasma flow rate or the correlation value of plasma flow rate is acquired with reference to the blood concentration detected from the patient's blood and the plasma total protein or the correlation value of plasma total protein calculated by the plasma-total-protein-acquiring unit. Therefore, the plasma total protein or the correlation value of plasma total protein can be calculated with reference to the colloid osmotic pressure or the correlation value of colloid osmotic pressure calculable by using the blood purification membrane in the blood purifier. Consequently, the plasma flow rate or the correlation value of plasma flow rate can be calculated easily.

Variations 4 and 11 may comprise the colloid osmotic pressure or the correlation value of colloid osmotic pressure is acquirable with reference to the transmembrane pressure difference calculated in the first step and the transmembrane pressure difference calculated in the second step. Therefore, the colloid osmotic pressure or the correlation value of colloid osmotic pressure can be calculated more smoothly by using the blood purification membrane in the blood purifier. Consequently, the plasma flow rate or the correlation value of plasma flow rate can be acquired easily with reference to the colloid osmotic pressure or the correlation value of colloid osmotic pressure.

Variations 5 and 12 may comprise the control unit sequentially executes the priming step in which the priming solution is supplied into the blood circuit and the treatment step in which blood purification treatment is performed with the blood purifier while the patient's blood is caused to extracorporeally circulate through the blood circuit. Furthermore, the liquid that does not generate colloid osmotic pressure and is supplied into the blood flow route in the first step is the priming solution that is used in the priming step, and the blood that is supplied into the blood flow route in the second step is the blood that is caused to extracorporeally circulate in the treatment step. Therefore, the colloid osmotic pressure or the correlation value of colloid osmotic pressure can be calculated accurately by efficiently utilizing the priming solution that is used in the priming step. Consequently, the plasma flow rate or the correlation value of plasma flow rate can be acquired easily with reference to the colloid osmotic pressure or the correlation value of colloid osmotic pressure.

Variations 6 and 13 may comprise the control unit executes the first step and the second step while the flow of the liquid is stopped in the blood flow route and in the dialysate flow route. Therefore, error factors (pressure loss and the like) that may occur with the flow of the liquid can be suppressed. Consequently, the colloid osmotic pressure or the correlation value of colloid osmotic pressure can be calculated more accurately. Furthermore, the plasma flow rate or the correlation value of plasma flow rate can be acquired easily with reference to the colloid osmotic pressure or the correlation value of colloid osmotic pressure.

Variations 7 and 14 may comprise the blood purification apparatus further includes the blood-concentration-detecting unit provided to the blood circuit and that detects the concentration of the blood flowing through the blood circuit on a time-course basis. Furthermore, the plasma flow rate or the correlation value of plasma flow rate is acquired with reference to the blood concentration detected on a time-course basis by the blood-concentration-detecting unit. Therefore, both the blood concentration and the plasma total protein that are required in acquiring the plasma flow rate or the correlation value of plasma flow rate can be detected during the blood purification treatment.

BRIEF DESCRIPTION OF THE DRAWINGS

FIG. 1 is a schematic diagram of a dialysis apparatus (a blood purification apparatus) according to a first embodiment of the present invention.

FIG. 2 is a flow chart of a control process executed by the dialysis apparatus.

FIG. 3 is a schematic diagram of the dialysis apparatus in a state established for a priming step.

FIG. 4 is a schematic diagram of the dialysis apparatus in a state established for a first step.

FIG. 5 is a schematic diagram of the dialysis apparatus in a state established for a treatment step.

FIG. 6 is a schematic diagram of the dialysis apparatus in a state established for a second step.

FIG. 7 is a schematic diagram of the dialysis apparatus in a state established for a modified second step.

FIG. 8 is a flow chart of a control process executed by a dialysis apparatus (a blood purification apparatus) according to a second embodiment of the present invention.

FIG. 9 is a schematic diagram of a dialysis apparatus (a blood purification apparatus) according to another embodiment of the present invention (in which pre-substitution is performed).

FIG. 10 is a schematic diagram of a dialysis apparatus (a blood purification apparatus) according to yet another embodiment of the present invention (in which physiological saline is employed as a priming solution).

FIG. 11 is a schematic diagram of a dialysis apparatus (a blood purification apparatus) according to yet another embodiment of the present invention (in which plasma total protein is detected).

DETAILED DESCRIPTION

Embodiments of the present invention will now be described specifically with reference to the drawings.

A blood purification apparatus according to a first embodiment is a dialysis apparatus for giving dialysis treatment and includes, as illustrated in FIG. 1, a blood circuit including an arterial blood circuit 1 and a venous blood circuit 2, a dialyzer 3 (a blood purifier) that purifies blood flowing through the blood circuit, an arterial air-trap chamber 5 connected to the arterial blood circuit 1, a venous air-trap chamber 6 connected to the venous blood circuit 2, a duplex pump 7, an ultrafiltration pump 8 (an ultrafiltration unit), a control unit 10, a colloid-osmotic-pressure-acquiring unit 11, a plasma-total-protein-acquiring unit 12, a plasma-flow-rate-acquiring unit 13, a substitution-rate-acquiring unit 14, a display 15, and a storage unit 16.

The arterial blood circuit 1 is provided with an arterial puncture needle (a) connected to a distal end thereof through a connector (c). A peristaltic blood pump 4 and the arterial air-trap chamber 5 are provided at respective halfway positions of the arterial blood circuit 1. The venous blood circuit 2 is provided with a venous puncture needle (b) connected to a distal end thereof through a connector (d). The venous air-trap chamber 6 is connected to a halfway position of the venous blood circuit 2. Furthermore, a distal portion (near the connector (c)) of the arterial blood circuit 1 and a distal portion (near the connector (d)) of the venous blood circuit 2 are provided with an electromagnetic valve V1 and an electromagnetic valve V2, respectively, which are capable of arbitrarily closing or opening respective flow routes.

In the dialysis treatment, when the blood pump 4 is activated while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 and returns into the patient's body. That is, the dialysis treatment (blood purification treatment) is performed by purifying the patient's blood with the dialyzer 3 while causing the blood to extracorporeally circulate through the blood circuit from the distal end of the arterial blood circuit 1 to the distal end of the venous blood circuit 2. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The arterial air-trap chamber 5 is provided with an overflow line La. The overflow line La extends from the top of the arterial air-trap chamber 5, with a distal end thereof open to the atmosphere. The overflow line La allows liquid (a priming solution) overflowing from the arterial air-trap chamber 5 to be discharged to the outside. The overflow line La is provided with an electromagnetic valve V3, which is capable of closing or opening a flow route as the overflow line La at an arbitrary timing.

The dialyzer 3 has, in a housing thereof, a blood inlet 3a (a blood introduction port), a blood outlet 3b (a blood delivery port), a dialysate inlet 3c (a dialysate introduction port), and a dialysate outlet 3d (a dialysate delivery port). The blood inlet 3a is connected to a proximal end of the arterial blood circuit 1. The blood outlet 3b is connected to a proximal end of the venous blood circuit 2. The dialysate inlet 3c and the dialysate outlet 3d are connected to a dialysate introduction line L1 and a dialysate drain line L2, respectively, extending from a dialysis device.

The dialyzer 3 houses a plurality of hollow fibers 3e. The hollow fibers 3e form blood purification membranes for purifying blood. The dialyzer 3 has blood flow routes (each extending between the blood inlet 3a and the blood outlet 3b) through which the patient's blood flows and dialysate flow routes (each extending between the dialysate inlet 3c and the dialysate outlet 3d) through which dialysate flows. The blood flow routes and the dialysate flow routes are separated from each other by the hollow fibers 3e (blood purification membranes). The hollow fibers 3e forming blood purification membranes each have a number of microscopic holes (pores) extending therethrough from the outer surface to the inner surface, thereby forming a hollow fiber membrane. Impurities and the like contained in the blood are allowed to permeate through the membranes into the dialysate.

The duplex pump 7 is provided over the dialysate introduction line L1 and the dialysate drain line L2 in the dialysis device. The dialysate drain line L2 is provided with a bypass line L3 that bypasses the duplex pump 7. The bypass line L3 is provided with the ultrafiltration pump 8 (the ultrafiltration unit) for removing water from the patient's blood flowing through the blood flow routes in the dialyzer 3. With the activation of the ultrafiltration pump 8, the pressure in the dialysate flow routes can be made lower than (negative to) the pressure in the blood flow routes in the dialyzer 3. Therefore, water is filtered out from the blood in the blood flow routes through the hollow fibers 3e (the blood purification membranes) and is drained through the dialysate flow routes, whereby ultrafiltration is achieved. The dialysate drain line L2 is further provided with a bypass line L4 that bypasses the duplex pump 7 and the ultrafiltration pump 8. The bypass line L4 is provided with an electromagnetic valve V6, which is capable of closing or opening a flow route as the bypass line L4 at an arbitrary timing.

The dialysate introduction line L1 forms a flow route for introducing the dialysate into the dialyzer 3. One end of the dialysate introduction line L1 is connected to the dialysate inlet 3c of the dialyzer 3, and the other end is connected to a dialysate supply device (not illustrated) that prepares a dialysate at a predetermined concentration. The dialysate drain line L2 forms a flow route for delivering waste liquid drained from the dialyzer 3. One end of the dialysate drain line L2 is connected to the dialysate outlet 3d of the dialyzer 3, and the other end is connected to a drainage unit, not illustrated.

Hence, when the duplex pump 7 is activated, the dialysate supplied from the dialysate supply device flows through the dialysate introduction line L1 into the dialyzer 3, and further flows through the dialysate drain line L2 into the drainage unit. The dialysate introduction line L1 and the dialysate drain line L2 are provided with an electromagnetic valve V4 and an electromagnetic valve V5 near respective points of connection to the dialyzer 3. Therefore, the flow routes as the dialysate introduction line L1 and the dialysate drain line L2 are each closable or openable at an arbitrary timing.

A dialysate supply line Lb is connected at one end thereof to a connecting portion 9 defined at a predetermined position of the dialysate introduction line L1 between the duplex pump 7 and the dialyzer 3. The other end of the dialysate supply line Lb branches into a priming-solution supply line Lba and a substitution-fluid supply line Lbb. The dialysate supply line Lb is provided with a peristaltic substitution pump F (a substitution-fluid supply unit). When the substitution pump F is activated, the dialysate (the priming solution) in the dialysate introduction line L1 can be supplied into the blood circuit. The substitution pump F as the substitution-fluid supply unit is not limited to the one of a peristaltic type and may be a pump of another type that is capable of controlling the flow rate.

The priming-solution supply line Lba is continuous at one end thereof with the dialysate supply line Lb and is connected at the other end thereof to a predetermined position of the arterial blood circuit 1 between the blood pump 4 and the electromagnetic valve V1. The priming-solution supply line Lba is provided with an electromagnetic valve V7 capable of arbitrarily closing or opening the flow route thereof. When the substitution pump F is activated with the electromagnetic valve V7 open, the dialysate (the priming solution) in the dialysate introduction line L1 can be supplied into the arterial blood circuit 1.

The substitution-fluid supply line Lbb is continuous at one end thereof with the dialysate supply line Lb and is connected at the other end thereof to the venous air-trap chamber 6. The substitution-fluid supply line Lbb is provided with an electromagnetic valve V8 capable of arbitrarily closing or opening the flow route thereof. When the substitution pump F is activated with the electromagnetic valve V8 open, the dialysate (the priming solution) in the dialysate introduction line L1 can be supplied into the venous blood circuit 2 through the venous air-trap chamber 6.

Hence, to perform a priming step, the substitution pump F is activated with the electromagnetic valve V7 open and the electromagnetic valve V8 closed. Thus, the dialysate as the priming solution is supplied into the arterial blood circuit 1 through the dialysate introduction line L1 and the priming-solution supply line Lba. To perform a treatment step, the substitution pump F is activated with the electromagnetic valve V7 closed and the electromagnetic valve V8 open. Thus, the dialysate as the substitution fluid is supplied into the venous blood circuit 2 through the dialysate introduction line L1 and the substitution-fluid supply line Lbb (post-substitution).

That is, when the substitution pump F is activated in the priming step, the dialysate as the priming solution can be supplied into the blood circuit through the dialysate introduction line L1 and the priming-solution supply line Lba. On the other hand, when the substitution pump F is activated in the treatment step, the dialysate as the substitution fluid can be supplied into the blood circuit through the dialysate introduction line L1 and the substitution-fluid supply line Lbb. The driving speed of the substitution pump F is arbitrarily controllable by the control unit 10, so that the dialysate can be supplied into the blood circuit at a required flow rate.

The blood circuit according to the present embodiment is further provided with a hematocrit sensor S (a blood-concentration-detecting unit). The hematocrit sensor S is capable of detecting the concentration of the blood flowing through the blood circuit on a time-course basis and is, for example, a sensor capable of measuring the blood concentration with reference to a light-reception voltage generated at the reception of light reflected by the blood flowing through the blood circuit. With the hematocrit sensor S, the concentration of the blood that is in extracorporeal circulation, particularly the hematocrit value as the volume fraction of blood cells, can be successively measured and monitored during the treatment.

According to the present embodiment, detecting units (a blood-flow-route-side inlet-pressure-detecting unit P1, a blood-flow-route-side outlet-pressure-detecting unit P2, a dialysate-flow-route-side inlet-pressure-detecting unit P3, and a dialysate-flow-route-side outlet-pressure-detecting unit P4) that detect the transmembrane pressure difference occurring on the hollow fibers 3e (the blood purification membranes) under a pressure difference between the liquid in the blood flow routes and the liquid in the dialysate flow routes are provided near respective points of connection between the dialyzer 3 and the proximal end of the arterial blood circuit 1, the proximal end of the venous blood circuit 2, the one end of the dialysate introduction line L1, and the one end of the dialysate drain line L2.

That is, the detecting units include the blood-flow-route-side inlet-pressure-detecting unit P1 that detects the blood pressure at the inlet side with respect to the blood flow routes of the dialyzer 3, the blood-flow-route-side outlet-pressure-detecting unit P2 that detects the blood pressure at the outlet side with respect to the blood flow routes, the dialysate-flow-route-side inlet-pressure-detecting unit P3 that detects the dialysate pressure at the inlet side with respect to the dialysate flow routes of the dialyzer 3, and the dialysate-flow-route-side outlet-pressure-detecting unit P4 that detects the dialysate pressure at the outlet side with respect to the dialysate flow routes.

Letting the value detected by the blood-flow-route-side inlet-pressure-detecting unit P1 be PBi, the value detected by the blood-flow-route-side outlet-pressure-detecting unit P2 be PBo, the value detected by the dialysate-flow-route-side inlet-pressure-detecting unit P3 be PDi, and the value detected by the dialysate-flow-route-side outlet-pressure-detecting unit P4 be PDo, the transmembrane pressure difference (TMP) occurring on the hollow fibers 3e (the blood purification membranes) can be calculated through Math. 1 given below.

$$TMP=(PBi+PBo)/2-(PDi+PDo)/2 \qquad <\text{Math. 1}>$$

The control unit 10 is a microcomputer or the like provided in the dialysis device and controls the opening/closing of the electromagnetic valves V1 to V8 and the driving of the actuators (such as the blood pump 4, the duplex pump 7, the ultrafiltration pump 8, and the substitution pump F). The control unit 10 according to the present embodiment is capable of sequentially executing the priming step (see FIG. 3) in which the priming solution (in the present embodiment, the dialysate supplied through the priming-solution supply line Lba) is supplied into the blood circuit, the treatment step (see FIG. 5) in which dialysis treatment (blood purification treatment) is performed with the dialyzer 3 while the patient's blood is caused to extracorporeally circulate through the blood circuit, and a blood-return step in which the blood in the blood circuit is returned to the patient after the dialysis treatment.

The control unit 10 according to the present embodiment is capable of executing a first step (see FIG. 4) in which liquid that does not generate colloid osmotic pressure is supplied into the blood flow routes with the filtration by the ultrafiltration pump 8 (the ultrafiltration unit) withheld (with the ultrafiltration pump 8 stopped), and the transmembrane pressure difference (TMPa) is calculated by using the detecting units (P1 to P4); and a second step (see FIG. 6) in which the patient's blood is supplied into the blood flow routes with the filtration by the ultrafiltration pump 8 (the ultrafiltration unit) withheld (with the ultrafiltration pump 8 stopped), and the transmembrane pressure difference (TMPb) is calculated by using the detecting units (P1 to P4).

In the present embodiment, the liquid that does not generate colloid osmotic pressure and is supplied into the blood flow routes in the first step is the priming solution that is used in the priming step (in the present embodiment, the dialysate that is supplied through the priming-solution supply line Lba), and the blood that is supplied into the blood flow routes in the second step is the blood that is caused to extracorporeally circulate in the treatment step. Before the treatment step, a gas-purging step for supplying the dialysate into the dialysate flow routes in the dialyzer 3 is executed.

The colloid-osmotic-pressure-acquiring unit 11 acquires the colloid osmotic pressure (CP) of the blood in the blood flow routes with reference to the transmembrane pressure difference (TMPa) occurring when the liquid (the priming solution) that does not generate colloid osmotic pressure is supplied into the blood flow routes with the filtration by the ultrafiltration pump 8 withheld and the transmembrane pressure difference (TMPb) occurring when the patient's blood is supplied into the blood flow routes with the filtration by the ultrafiltration pump 8 withheld. In the present embodiment, the colloid-osmotic-pressure-acquiring unit 11 is capable of acquiring the colloid osmotic pressure (CP) by calculating the difference between TMPa and TMPb (TMPb−TMPa).

In the present embodiment, the colloid osmotic pressure is acquired by calculating the difference between TMPa and TMPb. Alternatively, the colloid osmotic pressure (CP) may be acquired with reference to, for example, a table summarizing the relationship between colloid osmotic pressure (CP) and each of TMPa and TMPb. Moreover, the colloid-osmotic-pressure-acquiring unit 11 is not limited to the one that acquires the colloid osmotic pressure (CP) and may be the one that acquires a correlation value of colloid osmotic pressure (such as the ratio between TMPa and TMPb, or a value obtained by multiplying the colloid osmotic pressure (CP) by a predetermined coefficient) through calculation, with reference to a table, or by any other like means.

The plasma-total-protein-acquiring unit 12 acquires the plasma total protein (TP), which tells the amount (g/dL) of proteins such as albumin contained in the blood, with reference to the colloid osmotic pressure or the correlation value of colloid osmotic pressure acquired by the colloid-osmotic-pressure-acquiring unit 11. In the present embodiment, TP is solved from the following relational expression.

$$CP(\text{colloid osmotic pressure}) = 2.1(TP) + 0.16(TP)^2 + 0.009(TP)^3$$

In the present embodiment, the plasma total protein is acquired by calculating TP through the above relational expression. Alternatively, the plasma total protein (TP) may be acquired with reference to, for example, a table summarizing the relationship between plasma total protein (TP) and colloid osmotic pressure (CP). Moreover, the plasma-total-protein-acquiring unit 12 is not limited to the one that acquires the plasma total protein (TP) and may be the one that acquires a correlation value of plasma total protein (such as a value obtained by multiplying the plasma total protein (TP) by a predetermined coefficient) through calculation, with reference to a table, or by any other like means.

The plasma-flow-rate-acquiring unit 13 acquires the plasma flow rate (Qpw) at which plasma is filterable from the patient's blood or a correlation value of plasma flow rate (Qpw) with reference to the blood concentration (Ht) detected from the patient's blood and the plasma total protein (TP) detected from the blood flowing through the blood circuit. Specifically, the plasma flow rate (Qpw) is calculable through Math. 2 given below. Therefore, if any blood concentration (Ht) as a parameter is inputted and the plasma total protein (TP) acquired by the plasma-total-protein-acquiring unit 12 is substituted into Math. 2, the plasma flow rate (Qpw) at which plasma is filterable from the patient's blood can be acquired.

$$Qpw = Qb \times (1 - Ht) \times (1 - 0.0107 \times TP) \qquad <\text{Math. 2}>$$

where Qb denotes blood flow rate (mL/min), Ht denotes hematocrit (%), and TP denotes plasma total protein (g/dL).

Among the above parameters, the blood flow rate Qb is calculable from the driving speed of the blood pump 4 controlled by the control unit 10. In the present embodiment, the value of blood concentration (Ht) as one of the parameters in Math. 2 is acquired through a blood test conducted in advance and is inputted through an input unit of the blood purification apparatus. Alternatively, the plasma flow rate (Qpw) at which plasma is filterable from the patient's blood or the correlation value of plasma flow rate (Qpw) may be acquired by substituting the blood concentration (Ht) detected on a time-course basis by the hematocrit sensor S (the blood-concentration-detecting unit) into Math. 2.

In the present embodiment, the plasma flow rate (Qpw) is calculated through Math. 2 given above. Alternatively, the plasma flow rate (Qpw) may be acquired with reference to, for example, a table summarizing the relationship among blood flow rate (Qb), blood concentration (Ht), and plasma total protein (TP). Moreover, the plasma-flow-rate-acquiring unit 13 is not limited to the one that acquires the plasma flow rate (Qpw) and may be the one that acquires a correlation value of plasma flow rate (Qpw) (such as a value obtained by multiplying the plasma flow rate (Qpw) by a predetermined coefficient) through calculation, with reference to a table, or by any other like means.

The present embodiment employs the substitution-rate-acquiring unit 14 that calculates the substitution rate (Qs) to be achieved by the substitution pump F (the substitution-fluid supply unit) with reference to the plasma flow rate (Qpw) or the correlation value of plasma flow rate (Qpw) acquired by the plasma-flow-rate-acquiring unit 13. Specifically, since ultrafiltration (UF) is performed by the ultrafiltration pump 8 (the ultrafiltration unit) during the treatment, the substitution-rate-acquiring unit 14 can calculate the substitution rate (Qs) through Math. 3 given below.

$$Qs = Qpw \times FF/100 - Quf \qquad <\text{Math. 3}>$$

where Qpw denotes plasma flow rate (mL/min) at which plasma is filterable, FF denotes filtration fraction (%), and Quf denotes ultrafiltration rate (mL/min).

The display 15 is a screen such as a liquid-crystal monitor and is capable of displaying the substitution rate (Qs) acquired by the substitution-rate-acquiring unit 14 and other like information. In addition to the substitution rate (Qs), the display 15 according to the present embodiment is capable of displaying the plasma flow rate (Qpw) or the correlation value of plasma flow rate (Qpw) acquired by the plasma-flow-rate-acquiring unit 13. Since the substitution rate (Qs) and the plasma flow rate (Qpw) or the correlation value of plasma flow rate (Qpw) are displayed on the display 15, medical workers including doctors can grasp an appropriate substitution rate (Qs) corresponding to the plasma flow rate determined for the patient.

The display 15 may display only the substitution rate (Qs). Alternatively, in addition to the substitution rate (Qs), the display 15 may be capable of displaying the colloid osmotic pressure (CP) or the correlation value of colloid osmotic pressure (CP) acquired by the colloid-osmotic-pressure-acquiring unit 11, or the plasma total protein (TP) or the correlation value of plasma total protein (TP) acquired by the plasma-total-protein-acquiring unit 12. With reference to the values displayed on the display 15, medical workers including doctors can estimate the condition of the patient.

The storage unit 16 is a storage medium and is capable of storing the substitution rate (Qs) acquired by the substitution-rate-acquiring unit 14, the plasma flow rate (Qpw) or the correlation value of plasma flow rate (Qpw) acquired by the plasma-flow-rate-acquiring unit 13, and the like. The substitution rate (Qs), the colloid osmotic pressure or the correlation value of colloid osmotic pressure, and the plasma total protein or the correlation value of plasma total protein stored in the storage unit 16 are each preferred to be linked to other pieces of patient information and may be transmitted to a server or the like capable of transmitting and receiving information to and from the dialysis apparatus.

Now, a control process executed by the control unit 10 according to the present embodiment will be described with reference to a flow chart illustrated in FIG. 2.

First, before the treatment, the priming step and the gas-purging step are executed (S1). This step, S1, is executed as follows. As illustrated in FIG. 3, the connector (c) and the connector (d) are connected to each other to make the respective flow routes communicate with each other. Then, with the electromagnetic valves V4, V5 and V8 closed, the electromagnetic valves V1 to V3, V6 and V7 are opened. Furthermore, the blood pump 4 and the duplex pump 7 are activated, with the ultrafiltration pump 8 stopped.

Accordingly, the dialysate (the priming solution) in the dialysate introduction line L1 flows through the priming-solution supply line Lba into the blood circuit and fills the blood circuit. Then, the dialysate (the priming solution) is discharged to the outside through the overflow line La. Thus, the priming step is achieved. Subsequently, with the electromagnetic valves V6 and V7 closed, the electromagnetic valves V4 and V5 are opened. Accordingly, the dialysate flows into the dialysate flow routes in the dialyzer 3. Thus, the gas-purging step is achieved.

Subsequently, the first step, S2, is executed in which liquid that does not generate colloid osmotic pressure (the priming solution used in the priming step in S1) is supplied into the blood flow routes with the filtration (ultrafiltration) by the ultrafiltration pump 8 (the ultrafiltration unit) withheld, and the transmembrane pressure difference (TMPa) is calculated by using the detecting units (P1 to P4). Specifically, the first step S2 is executed as follows. As illustrated in FIG. 4, with the electromagnetic valves V3, V6, V7, and V8 closed, the electromagnetic valves V1, V2, V4, and V5 are opened. Furthermore, with the blood pump 4 and the duplex pump 7 kept activated and the ultrafiltration pump 8 kept stopped, the transmembrane pressure difference (TMPa) is calculated from the values detected by the detecting units (P1 to P4).

Subsequently, the treatment step, S3, is executed in which blood purification treatment is performed with the dialyzer 3 while the patient's blood is caused to extracorporeally circulate through the blood circuit. The treatment step S3 is executed as follows. As illustrated in FIG. 5, the connector (c) and the connector (d) are disconnected from each other, and the arterial puncture needle (a) and the venous puncture needle (b) are connected thereto, respectively. Then, with the electromagnetic valves V3, V6, and V7 closed, the electromagnetic valves V1, V2, V4, and V5 are opened. Furthermore, the blood pump 4, the duplex pump 7, and the ultrafiltration pump 8 are activated.

Thus, the patient's blood is substituted for the priming solution (the dialysate) in the blood circuit and extracorporeally circulates therethrough. In the process of extracorporeal circulation, blood purification treatment is achieved with the dialyzer 3. Furthermore, since the ultrafiltration pump 8 is activated, water can be filtered out from the blood in the blood flow routes through the hollow fibers 3e (the blood purification membranes) and be drained through the dialysate flow routes. Thus, ultrafiltration is achieved.

Subsequently, in S4, whether or not a predetermined time has elapsed since the start of the treatment is checked. If it is determined that the predetermined time has elapsed, the ultrafiltration pump 8 is stopped to stop the filtration (ultrafiltration) (S5). Then, the second step, S6, is executed in which the patient's blood is supplied into the blood flow routes with the filtration (ultrafiltration) by the ultrafiltration pump 8 (the ultrafiltration unit) withheld, and the transmembrane pressure difference (TMPb) is calculated by using the detecting units (P1 to P4). Specifically, the second step S6 is executed as follows. As illustrated in FIG. 6, with the electromagnetic valves V3, V6, and V7 closed, the electromagnetic valves V1, V2, V4, V5, and V8 are opened. Furthermore, with the blood pump 4 and the duplex pump 7 kept activated and the ultrafiltration pump 8 stopped, the transmembrane pressure difference (TMPb) is calculated from the values detected by the detecting units (P1 to P4).

Subsequently, the colloid osmotic pressure (CP) or the correlation value of colloid osmotic pressure (CP) is acquired from TMPa and TMPb through calculation by the colloid-osmotic-pressure-acquiring unit 11 (S7). Furthermore, the plasma total protein (TP) or the correlation value of plasma total protein (TP) is acquired with reference to the colloid osmotic pressure (CP) or the correlation value of colloid osmotic pressure (CP) acquired as above, through calculation by the plasma-total-protein-acquiring unit 12 (S8). The colloid osmotic pressure (CP) or the correlation value of colloid osmotic pressure (CP) and the plasma total protein (TP) or the correlation value of plasma total protein (TP) acquired as above are displayed on the display 15 and stored in the storage unit 16 (S9).

Furthermore, the plasma flow rate (Qpw) or the correlation value of plasma flow rate (Qpw) is acquired through calculation by the plasma-flow-rate-acquiring unit 12 (S10). Then, the substitution rate (Qs) is acquired with reference to the plasma flow rate (Qpw) or the correlation value of plasma flow rate (Qpw) acquired as above, through calculation by the substitution-rate-acquiring unit 14 (S11). The substitution rate (Qs) and the plasma flow rate (Qpw) or the correlation value of plasma flow rate (Qpw) acquired as above are displayed on the display 15 and stored in the storage unit 16.

As described above, in the present embodiment, the plasma flow rate (Qpw) at which plasma is filterable from the patient's blood or the correlation value of plasma flow rate (Qpw) can be acquired with reference to the blood concentration detected from the patient's blood and the plasma total protein (TP) detected from the blood flowing through the blood circuit, and the substitution rate (Qs) can be calculated from the plasma flow rate (Qpw) or the correlation value of plasma flow rate (Qpw). Therefore, the substitution pump F can be controlled such that the calculated substitution rate (Qs) is achieved. The substitution pump F may be controlled automatically by the control unit 10 or manually such that the substitution rate (Qs) displayed on the display 15 is achieved.

In each of the first step S2 and the second step S6, the control unit 10 according to the present embodiment operates such that the transmembrane pressure difference (TMPa or TMPb) is calculated with the blood pump 4 and the duplex pump 7 activated. Alternatively, the transmembrane pressure difference (TMPa or TMPb) may be calculated with the blood pump 4 and the duplex pump 7 stopped. In the latter case, the second step S6, for example, is executed as follows (the same applies to the first step S2). As illustrated in FIG. 7, the electromagnetic valves V3, V6, and V7 are closed; the electromagnetic valves V1, V2, V4, V5, and V8 are opened; and the blood pump 4, the duplex pump 7, and the ultrafiltration pump 8 are stopped.

In the above control process, the first step S2 and the second step S6 can be executed while the flow of the liquid is stopped in the blood flow routes and in the dialysate flow routes. Therefore, error factors, such as pressure loss due to the flow of the liquid in the blood flow routes and in the dialysate flow routes and the occurrence of filtration due to unbalanced driving of the duplex pump 7, can be suppressed. Consequently, the colloid osmotic pressure or the correlation value of colloid osmotic pressure (and the plasma total protein or the correlation value of plasma total protein, the plasma flow rate (Qpw) or the correlation value of plasma flow rate (Qpw), and the substitution rate (Qs)) can be calculated more accurately.

Furthermore, since the flow of the liquid is stopped in the blood flow routes and in the dialysate flow routes, hydraulic pressures at a position of the arterial blood circuit 1 that is on the upstream (inlet) side of the dialyzer 3, a position of the venous blood circuit 2 that is on the downstream (outlet) side of the dialyzer 3, a position of the dialysate introduction line L1 that is on the upstream (inlet) side of the dialyzer 3, and a position of the dialysate drain line L2 that is on the downstream (outlet) side of the dialyzer 3 become substantially equal. Therefore, TMPa or TMPb can be calculated from one of the value detected by the blood-flow-route-side inlet-pressure-detecting unit P1 and the value detected by the blood-flow-route-side outlet-pressure-detecting unit P2, and one of the value detected by the dialysate-flow-route-side inlet-pressure-detecting unit P3 and the value detected by the dialysate-flow-route-side outlet-pressure-detecting unit P4.

According to the present embodiment, the plasma flow rate (Qpw) at which plasma is filterable from the patient's blood or the correlation value of plasma flow rate (Qpw) is acquired with reference to the blood concentration (Ht) detected from the patient's blood and the plasma total protein (TP) detected from the blood flowing through the blood circuit. Therefore, the plasma flow rate (Qpw) at which plasma is filterable from the patient's blood or the correlation value of plasma flow rate (Qpw) can be calculated accurately by detecting the plasma total protein (TP) from the blood flowing through the blood circuit during the blood purification treatment.

In particular, according to the present embodiment, the substitution rate (Qs) to be achieved by the substitution pump F (the substitution-fluid supply unit) is calculated with reference to the plasma flow rate (Qpw) or the correlation value of plasma flow rate (Qpw). Therefore, substitution can be achieved at a substitution rate (Qs) that is optimum for the plasma flow rate (Qpw) or the correlation value of plasma flow rate (Qpw). While the present embodiment employs the substitution-rate-acquiring unit 14 to calculate the substitution rate (Qs), the substitution-rate-acquiring unit 14 may be omitted. Instead, medical workers including doctors may calculate an appropriate substitution rate (Qs) with reference to the plasma flow rate (Qpw) or the correlation value of plasma flow rate (Qpw) acquired by the plasma-flow-rate-acquiring unit 13.

The present embodiment further employs the detecting units (P1 to P4), the colloid-osmotic-pressure-acquiring unit 11, and the plasma-total-protein-acquiring unit 12, so that the plasma flow rate (Qpw) at which plasma is filterable from the patient's blood or the correlation value of plasma flow rate (Qpw) is acquired with reference to the blood concentration (Ht) detected from the patient's blood and the plasma total protein (TP) or the correlation value of plasma total protein (TP) calculated by the plasma-total-protein-acquiring unit 12. Therefore, the plasma total protein (TP) or the correlation value of plasma total protein (TP) can be calculated with reference to the colloid osmotic pressure (CP) or the correlation value of colloid osmotic pressure (CP) calculable by using the hollow fibers 3e (the blood purification membranes) in the dialyzer 3 (the blood purifier). Consequently, the plasma flow rate (Qpw) at which plasma is filterable from the patient's blood or the correlation value of plasma flow rate (Qpw) can be calculated easily.

Furthermore, the colloid osmotic pressure (CP) or the correlation value of colloid osmotic pressure (CP) is acquired with reference to the transmembrane pressure difference (TMPa) calculated in the first step S2 and the transmembrane pressure difference (TMPb) calculated in the second step S6. Therefore, the colloid osmotic pressure (CP) or the correlation value of colloid osmotic pressure (CP) can be calculated more smoothly by using the hollow fibers 3e (the blood purification membranes) in the dialyzer 3 (the blood purifier). Consequently, the plasma flow rate (Qpw) at which plasma is filterable from the patient's blood or the correlation value of plasma flow rate (Qpw) can be acquired easily with reference to the colloid osmotic pressure (CP) or the correlation value of colloid osmotic pressure (CP).

Furthermore, the control unit 10 according to the present embodiment is capable of sequentially executing the priming step in which the priming solution is supplied into the blood circuit and the treatment step in which blood purification treatment is performed with the dialyzer 3 (the blood purifier) while the patient's blood is caused to extracorporeally circulate through the blood circuit. Furthermore, the liquid that does not generate colloid osmotic pressure (CP) and is supplied into the blood flow routes in the first step S2 is the priming solution that is used in the priming step, and the blood that is supplied into the blood flow routes in the second step S6 is the blood that is caused to extracorporeally circulate in the treatment step. Therefore, the colloid osmotic pressure (CP) or the correlation value of colloid osmotic pressure (CP) can be calculated accurately by efficiently utilizing the priming solution that is used in the priming step. Consequently, the plasma flow rate (Qpw) at which plasma is filterable from the patient's blood or the correlation value of plasma flow rate (Qpw) (and the substitution rate (Qs)) can be acquired easily with reference to the colloid osmotic pressure (CP) or the correlation value of colloid osmotic pressure (CP).

If the hematocrit sensor S (the blood-concentration-detecting unit) provided to the blood circuit and capable of detecting blood concentration (Ht) of the blood flowing through the blood circuit on a time-course basis is employed and the plasma flow rate (Qpw) at which plasma is filterable from the patient's blood or the correlation value of plasma flow rate (Qpw) is acquired with reference to the blood concentration (Ht) detected on a time-course basis by the hematocrit sensor S, both the blood concentration (Ht) and the plasma total protein (TP) that are required in acquiring the plasma flow rate (Qpw) at which plasma is filterable from the patient's blood or the correlation value of plasma flow rate (Qpw) can be detected during the blood purification treatment.

Now, a second embodiment of the present invention will be described.

As with the case of the first embodiment, a blood purification apparatus according to the present embodiment is a dialysis apparatus for giving dialysis treatment and includes, as illustrated in FIG. 1, a blood circuit including an arterial blood circuit 1 and a venous blood circuit 2, a dialyzer 3 (a blood purifier) that purifies blood flowing through the blood circuit, an arterial air-trap chamber 5 connected to the arterial blood circuit 1, a venous air-trap chamber 6 connected to the venous blood circuit 2, a duplex pump 7, an ultrafiltration pump 8 (an ultrafiltration unit), a control unit 10, a colloid-osmotic-pressure-acquiring unit 11, a plasma-total-protein-acquiring unit 12, a plasma-flow-rate-acquiring unit 13, a substitution-rate-acquiring unit 14, a display 15, and a storage unit 16. The configuration of the apparatus is the same as that described in the first embodiment, and detailed description thereof is omitted.

In the present embodiment, the blood circuit is fixed at a predetermined position, and the detecting units (P1 to P4) are provided at respective predetermined positions. The storage unit 16 is capable of storing, as a theoretical value, the transmembrane pressure difference (TMPa) occurring when the liquid that does not generate colloid osmotic pressure (the dialysate as the priming solution) is supplied into the blood flow routes with the filtration by the ultrafiltration pump 8 (the ultrafiltration unit) withheld. The colloid-osmotic-pressure-acquiring unit 11 is capable of acquiring the colloid osmotic pressure of the blood in the blood flow routes or the correlation value of colloid osmotic pressure with reference to the above theoretical value and the transmembrane pressure difference (TMPb) occurring when the patient's blood is supplied into the blood flow routes with the filtration by the ultrafiltration pump 8 (the ultrafiltration unit) withheld.

Now, a control process executed by the control unit 10 according to the present embodiment will be described with reference to a flow chart illustrated in FIG. 8.

First, the transmembrane pressure difference (TMPa) occurring when the liquid that does not generate colloid osmotic pressure is supplied into the blood flow routes with the filtration by the ultrafiltration pump 8 withheld is stored as a theoretical value in advance in the storage unit 16. Then, before the treatment, the priming step and the gas-purging step are executed (S1). This step, S1, is executed as follows. As illustrated in FIG. 3, the connector (c) and the connector (d) are connected to each other to make the respective flow routes communicate with each other. Then, with the electromagnetic valves V4, V5, and V8 closed, the electromagnetic valves V1 to V3, V6, and V7 are opened. Furthermore, the blood pump 4 and the duplex pump 7 are activated, with the ultrafiltration pump 8 stopped.

Accordingly, the dialysate (the priming solution) in the dialysate introduction line L1 flows through the priming-solution supply line Lba into the blood circuit and fills the blood circuit. Then, the dialysate (the priming solution) is discharged to the outside through the overflow line La. Thus, the priming step is achieved. Subsequently, with the electromagnetic valves V6, V7, and V8 closed, the electromagnetic valves V4 and V5 are opened. Accordingly, the dialysate flows into the dialysate flow routes in the dialyzer 3. Thus, the gas-purging step is achieved.

Subsequently, the treatment step, S2, is executed in which blood purification treatment is performed with the dialyzer 3 while the patient's blood is caused to extracorporeally circulate through the blood circuit. The treatment step S2 is executed as follows. As illustrated in FIG. 5, the connector (c) and the connector (d) are disconnected from each other, and the arterial puncture needle (a) and the venous puncture needle (b) are connected thereto, respectively. Then, with the electromagnetic valves V3, V6, and V7 closed, the electromagnetic valves V1, V2, V4, V5, and V8 are opened. Furthermore, the blood pump 4, the duplex pump 7, and the ultrafiltration pump 8 are activated.

Thus, the patient's blood is substituted for the priming solution (the dialysate) in the blood circuit and extracorporeally circulates therethrough. In the process of extracorporeal circulation, blood purification treatment is achieved with the dialyzer 3. Furthermore, since the ultrafiltration pump 8 is activated, water can be filtered out from the blood in the blood flow routes through the hollow fibers 3e (the blood purification membranes) and be drained through the dialysate flow routes. Thus, ultrafiltration can be achieved.

Subsequently, in S3, whether or not a predetermined time has elapsed since the start of the treatment is checked. If it is determined that the predetermined time has elapsed, the ultrafiltration pump 8 is stopped to stop the filtration (ultrafiltration) (S4). Then, the second step, S5, is executed in which the patient's blood is supplied into the blood flow routes with the filtration (ultrafiltration) by the ultrafiltration pump 8 (the ultrafiltration unit) withheld, and the transmembrane pressure difference (TMPb) is calculated by using the detecting units (P1 to P4). Specifically, the second step S5 is executed as follows. As illustrated in FIG. 6, with the electromagnetic valves V3, V6, and V7 closed, the electromagnetic valves V1, V2, V4, V5, and V8 are opened. Furthermore, with the blood pump 4 and the duplex pump 7 kept activated and the ultrafiltration pump 8 stopped, the transmembrane pressure difference (TMPb) is calculated from the values detected by the detecting units (P1 to P4).

Subsequently, the colloid osmotic pressure (CP) or the correlation value of colloid osmotic pressure (CP) is acquired from TMPa, which is the prestored theoretical value, and TMPb, which is the actual measured value, through calculation by the colloid-osmotic-pressure-acquiring unit 11 (S6). Furthermore, the plasma total protein (TP) or the correlation value of plasma total protein (TP) is acquired with reference to the colloid osmotic pressure (CP) or the correlation value of colloid osmotic pressure (CP) acquired as above, through calculation by the plasma-total-protein-acquiring unit 12 (S7). The colloid osmotic pressure (CP) or the correlation value of colloid osmotic pressure (CP) and the plasma total protein (TP) or the correlation value of plasma total protein (TP) acquired as above are displayed on the display 15 and stored in the storage unit 16 (S8).

Furthermore, the plasma flow rate (Qpw) or the correlation value of plasma flow rate (Qpw) is acquired through calculation by the plasma-flow-rate-acquiring unit 12 (S9). Then, the substitution rate (Qs) is acquired with reference to the plasma flow rate (Qpw) or the correlation value of plasma flow rate (Qpw) acquired as above, through calculation by the substitution-rate-acquiring unit 14 (S10). The substitution rate (Qs) and the plasma flow rate (Qpw) or the correlation value of plasma flow rate (Qpw) acquired as above are displayed on the display 15 and stored in the storage unit 16.

As described above, in the present embodiment, the plasma flow rate (Qpw) at which plasma is filterable from the patient's blood or the correlation value of plasma flow rate (Qpw) can be acquired with reference to the blood concentration detected from the patient's blood and the plasma total protein (TP) detected from the blood flowing through the blood circuit, and the substitution rate (Qs) can be calculated from the plasma flow rate (Qpw) or the correlation value of plasma flow rate (Qpw). Therefore, the substitution pump F can be controlled such that the calculated substitution rate (Qs) is achieved. The substitution pump F may be controlled automatically by the control unit 10 or manually such that the substitution rate (Qs) displayed on the display 15 is achieved.

According to the present embodiment, the detecting units (P1 to P4) are provided at the respective predetermined positions. Furthermore, the transmembrane pressure difference (TMPa) occurring when the liquid that does not generate colloid osmotic pressure is supplied into the blood flow routes with the filtration by the ultrafiltration pump 8 (the ultrafiltration unit) withheld is stored as a theoretical value. Furthermore, the colloid osmotic pressure of the blood in the blood flow routes or the correlation value of colloid osmotic pressure is acquired with reference to the above theoretical value and the transmembrane pressure difference (TMPb) occurring when the patient's blood is supplied into the blood flow routes with the filtration by the ultrafiltration pump 8 (the ultrafiltration unit) withheld. Therefore, it is not necessary to acquire the transmembrane pressure difference (TMPa) as the actual measured value. Consequently, not only the colloid osmotic pressure (CP) or the correlation value of colloid osmotic pressure (CP) but also the plasma flow rate (Qpw) or the correlation value of plasma flow rate (Qpw) and the substitution rate (Qs) can be calculated more easily.

While some embodiments have been described above, the present invention is not limited thereto. For example, as illustrated in FIG. 9, the other end of the substitution-fluid supply line Lbb may be connected to the arterial air-trap chamber 5 so that the dialysate as the substitution fluid can be supplied into the arterial blood circuit 1 (for pre-substitution). In such a case where pre-substitution is performed, the plasma-flow-rate-acquiring unit 13 can calculate the plasma flow rate (Qpw) through Math. 4 given below, and the substitution-rate-acquiring unit 14 can calculate the substitution rate (Qs) through Math. 5 given below.

$$Qpw=(100-Ht)/100\times(1-0.00107\times TP)\times Qb \qquad \text{<Math. 4>}$$

$$Qs=(Qpw\times FF/100-Quf)/(1-FF/100) \qquad \text{<Math. 5>}$$

where Qpw denotes plasma flow rate (mL/min) at which plasma is filterable, Qb denotes blood flow rate (mL/min), Ht denotes hematocrit (%), TP denotes plasma total protein, FF denotes filtration fraction (%), and Quf denotes ultrafiltration rate (mL/min).

Alternatively, as illustrated in FIG. 10, the priming-solution supply line Lba may be replaced with a priming-solution supply line Lc connected to a bag D (a saline bag) storing physiological saline, so that the physiological saline can be supplied as the priming solution. In such a case, the liquid that does not generate colloid osmotic pressure is preferred to be the physiological saline as the priming solution. The liquid that does not generate colloid osmotic pressure may be another kind of liquid different from dialysate or physiological saline.

The acquisition of the colloid osmotic pressure (CP) or the correlation value of colloid osmotic pressure (CP), the plasma flow rate (Qpw) or the correlation value of plasma flow rate (Qpw), and the substitution rate (Qs) is not limited to be executed once in an early stage of the treatment. The second step may be executed plural times during the treatment, so that the colloid osmotic pressure (CP) or the correlation value of colloid osmotic pressure (CP), the plasma flow rate (Qpw) or the correlation value of plasma flow rate (Qpw), and the substitution rate (Qs) are acquired each of the plural times.

As another alternative, as illustrated in FIG. 11, the blood circuit (in the drawing, the arterial blood circuit 1) may be provided with a sensor W capable of detecting the plasma total protein (TP) on a time-course basis or intermittently. In such a case, the sensor W is preferred to be capable of detecting the plasma total protein (TP) by, for example, emitting light, ultrasonic waves, or the like to the blood flowing through the blood circuit and receiving the light, ultrasonic waves, or the like reflected by or transmitted through the blood. In such an embodiment, there is no need to acquire the colloid osmotic pressure (CP) in calculating the plasma flow rate (Qpw) and the substitution rate (Qs). Therefore, the plasma flow rate (Qpw) at which plasma is filterable or the correlation value of plasma flow rate (Qpw) and the substitution rate (Qs) can be calculated more smoothly.

While the above embodiments are each applied to a dialysis apparatus intended for dialysis treatment, the present invention may also be applied to another apparatus (such as a blood purification apparatus intended for hemofiltration) that is capable of purifying a patient's blood while causing the blood to extracorporeally circulate.

The present invention is applicable to any blood purification apparatus and any method of acquiring the plasma flow rate on a blood purification apparatus that are in any other mode and for any other use, as long as the plasma flow rate or the correlation value of plasma flow rate is acquired with reference to the blood concentration detected from a patient's blood and the plasma total protein detected from the blood flowing through a blood circuit.

REFERENCE SIGN LIST

1 arterial blood circuit
2 venous blood circuit
3 dialyzer (blood purifier)
3a blood inlet
3b blood outlet
3c dialysate inlet
3d dialysate outlet
3e hollow fiber (blood purification membrane)
4 blood pump
5 arterial air-trap chamber
6 venous air-trap chamber
7 duplex pump
8 ultrafiltration pump (ultrafiltration unit)
9 connecting portion
10 control unit
11 colloid-osmotic-pressure-acquiring unit
12 plasma-total-protein-acquiring unit
13 plasma-flow-rate-acquiring unit
14 substitution-rate-acquiring unit
15 display
16 storage unit F substitution pump (substitution-fluid supply unit)
S hematocrit sensor (blood-concentration-detecting unit)
P1 blood-flow-route-side inlet-pressure-detecting unit
P2 blood-flow-route-side outlet-pressure-detecting unit
P3 dialysate-flow-route-side inlet-pressure-detecting unit
P4 dialysate-flow-route-side outlet-pressure-detecting unit
L1 dialysate introduction line
L2 dialysate drain line
L3 bypass line
L4 bypass line
La overflow line
Lb dialysate supply line
Lba priming-solution supply line
Lbb substitution-fluid supply line
W sensor (for plasma total protein)

The invention claimed is:

1. A blood purification apparatus comprising:
a blood circuit including an arterial blood circuit and a venous blood circuit and that allows a patient's blood to extracorporeally circulate from a distal end of the arterial blood circuit to a distal end of the venous blood circuit;
a blood purifier provided between the arterial blood circuit and the venous blood circuit and that purifies the patient's blood flowing through the blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
an ultrafiltration unit that performs ultrafiltration by filtering out water from the patient's blood in the blood flow route through the blood purification membrane and draining the water through the dialysate flow route; and
a substitution-fluid supply unit that supplies substitution fluid into the blood circuit, and
a detecting unit that detects a transmembrane pressure difference occurring on the blood purification membrane under a pressure difference between liquid in the blood flow route and liquid in the dialysate flow route;
the blood purification apparatus comprising:
a colloid-osmotic-pressure-acquiring unit that acquires a colloid osmotic pressure of the patient's blood in the blood flow route or a correlation value of colloid osmotic pressure with reference to the transmembrane pressure difference occurring when liquid that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;
a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit,
a plasma-flow-rate-acquiring unit that acquires a plasma flow rate or a correlation value of plasma flow rate with reference to a blood concentration detected from the patient's blood and the plasma total protein or the correlation value of the plasma total protein acquired by the plasma total protein acquiring unit; and
a control unit in communication with and controlling the colloid-osmotic-pressure-acquiring unit, the plasma-total-protein-acquiring unit, and the plasma-flow-rate-acquiring unit;
wherein a substitution rate to be achieved by the substitution-fluid supply unit is calculated with reference to the plasma flow rate or the correlation value of plasma flow rate acquired by the plasma-flow-rate-acquiring unit; and
wherein the plasma flow rate (Qpw) is determined with a formula comprising: $Qpw=Qb*(1-Ht)*(1-0.0107*TP)$ where Qb is a blood flow rate in mL/min, Ht denotes a hematocrit percentage and TP is the plasma total protein.

2. The blood purification apparatus according to claim 1, wherein the control unit executes
a first step in which the liquid that does not generate colloid osmotic pressure is supplied into the blood flow route with the filtration by the ultrafiltration unit withheld, and the transmembrane pressure difference is calculated by using the detecting unit; and
a second step in which the patient's blood is supplied into the blood flow route with the filtration by the ultrafiltration unit withheld, and the transmembrane pressure difference is calculated by using the detecting unit,
wherein the colloid-osmotic-pressure-acquiring unit acquires the colloid osmotic pressure or the correlation value of colloid osmotic pressure with reference to the transmembrane pressure difference calculated in the first step and the transmembrane pressure difference calculated in the second step.

3. The blood purification apparatus according to claim 2, wherein the control unit is capable of sequentially executing a priming step in which a priming solution is supplied into the blood circuit and a treatment step in which blood purification treatment is performed with the blood purifier while the patient's blood is caused to extracorporeally circulate through the blood circuit; the liquid that does not generate colloid osmotic pressure and is supplied into the blood flow route in the first step is the priming solution that is used in the priming step; and the blood that is supplied into the blood flow route in the second step is the blood that is caused to extracorporeally circulate in the treatment step.

4. The blood purification apparatus according to claim 2, wherein the control unit executes the first step and the second step while a flow of the liquid is stopped in the blood flow route and a flow of the liquid is stopped in the dialysate flow route.

5. The blood purification apparatus according to claim 1, further comprising a blood-concentration-detecting unit provided to the blood circuit and that detects a concentration of the blood flowing through the blood circuit on a time-course basis, wherein the plasma-flow-rate-acquiring unit acquires the plasma flow rate or the correlation value of plasma flow rate with reference to the concentration of the blood detected on a time-course basis by the blood-concentration-detecting unit.

6. A blood purification apparatus according to claim 1, wherein the substitution-fluid supply unit comprises a substitution pump that supplies dialysate in a dialysate introduction line into the blood circuit as the substitution fluid.

7. The blood purification apparatus according to claim 1, wherein the plasma total protein (TP) is determined with a formula comprising: $CP=2.1\ (TP)+0.16(TP)^2+0.009(TP)^3$, where CP is colloid osmotic pressure.

8. A method of acquiring a plasma flow rate on a blood purification apparatus, the blood purification apparatus comprising:
- extracorporeally circulating a patient's blood from a distal end of an arterial blood circuit to a distal end of a venous blood circuit of a blood circuit;
- purifying the patient's blood through a blood purifier provided between the arterial blood circuit and the venous blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
- performing ultrafiltration with an ultrafiltration unit that filters out water from the patient's blood in the blood flow route through the blood purification membrane and draining the water through the dialysate flow route;
- supplying substitution fluid with a substitution-fluid supply unit that supplies the substitution fluid into the blood circuit,
- detecting, with a detecting unit, a transmembrane pressure difference occurring on the blood purification membrane under a pressure difference between liquid in the blood flow route and liquid in the dialysate flow route;
- acquiring a colloid osmotic pressure of the patient's blood, with a colloid-osmotic-pressure-acquiring unit, in the blood flow route or a correlation value of colloid osmotic pressure with reference to the transmembrane pressure difference occurring when liquid in the blood flow route that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;
- acquiring, with a plasma-total-protein-acquiring unit, a plasma total protein or a correlation value of plasma total protein with reference to the colloid osmotic pressure or the correlation value of colloid osmotic pressure acquired by the colloid-osmotic-pressure-acquiring unit;
- acquiring, with a plasma-flow-rate-acquiring unit, the plasma flow rate or a correlation value of plasma flow rate with reference to a blood concentration detected from the patient's blood and the plasma total protein or the correlation value of the plasma total protein acquired by the plasma-total-protein-acquiring unit;
- calculating, with reference to the plasma flow rate or the correlation value of plasma flow rate acquired by a plasma-flow-rate-acquiring unit, a substitution rate to be achieved by the substitution-fluid supply unit; and
- controlling the colloid-osmotic-pressure-acquiring unit, the plasma-total-protein-acquiring unit, and the plasma-flow-rate-acquiring unit with a control unit;
- wherein the plasma flow rate (Qpw) is determined with a formula comprising: $Qpw=Qb*(1-Ht)*(1-0.0107*TP)$ where Qb is a blood flow rate in mL/min, Ht denotes a hematocrit percentage and TP is the plasma total protein.

9. The method of acquiring the plasma flow rate on the blood purification apparatus according to claim 8, wherein the control unit executes
- a first step in which the liquid that does not generate colloid osmotic pressure is supplied into the blood flow route with the filtration by the ultrafiltration unit withheld, and the transmembrane pressure difference is calculated by using the detecting unit; and
- a second step in which the patient's blood is supplied into the blood flow route with the filtration by the ultrafiltration unit withheld, and the transmembrane pressure difference is calculated by using the detecting unit,
- wherein the colloid osmotic pressure or the correlation value of colloid osmotic pressure is acquired with reference to the transmembrane pressure difference calculated in the first step and the transmembrane pressure difference calculated in the second step.

10. The method of acquiring the plasma flow rate on the blood purification apparatus according to claim 9, wherein the control unit sequentially executes a priming step in which a priming solution is supplied into the blood circuit and a treatment step in which blood purification treatment is performed with the blood purifier while the patient's blood is caused to extracorporeally circulate through the blood circuit; the liquid that does not generate colloid osmotic pressure and is supplied into the blood flow route in the first step is the priming solution that is used in the priming step; and the blood that is supplied into the blood flow route in the second step is the blood that is caused to extracorporeally circulate in the treatment step.

11. The method of acquiring the plasma flow rate on the blood purification apparatus according to claim 9, wherein the control unit executes the first step and the second step while a flow of the liquid in the blood flow route is stopped in the blood flow route and a flow of the liquid in the dialysate flow route is stopped in the dialysate flow route.

12. The method of acquiring the plasma flow rate on blood purification apparatus according to claim 8, wherein the blood purification apparatus further includes a blood-concentration-detecting unit provided to the blood circuit and that is capable of detecting a concentration of the blood flowing through the blood circuit on a time-course basis, wherein the plasma flow rate or the correlation value of plasma flow rate is acquired with reference to the concentration of the blood detected on a time-course basis by the blood-concentration-detecting unit.

13. A blood purification apparatus comprising:
- a blood circuit including an arterial blood circuit and a venous blood circuit and that allows a patient's blood to extracorporeally circulate from a distal end of the arterial blood circuit to a distal end of the venous blood circuit;
- a blood purifier provided between the arterial blood circuit and the venous blood circuit and that purifies the patient's blood flowing through the blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
- an ultrafiltration unit that performs ultrafiltration by filtering out water from the patient's blood in the blood flow route through the blood purification membrane and draining the water through the dialysate flow route; and
- a substitution-fluid supply unit that supplies substitution fluid into the blood circuit, and
- a detecting unit that detects a transmembrane pressure difference occurring on the blood purification membrane under a pressure difference between liquid in the blood flow route and liquid in the dialysate flow route;

the blood purification apparatus comprising:
a colloid-osmotic-pressure-acquiring unit that acquires a colloid osmotic pressure of the patient's blood in the blood flow route or a correlation value of colloid osmotic pressure with reference to the transmembrane pressure difference occurring when liquid that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;
a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit,
a plasma-flow-rate-acquiring unit that acquires a plasma flow rate or a correlation value of plasma flow rate with reference to a blood concentration detected from the patient's blood and the plasma total protein or the correlation value of the plasma total protein acquired by the plasma total protein acquiring unit; and
a control unit in communication with and controlling the colloid-osmotic-pressure-acquiring unit, the plasma-total-protein-acquiring unit, and the plasma-flow-rate-acquiring unit; wherein a substitution rate to be achieved by the substitution-fluid supply unit is calculated with reference to the plasma flow rate or the correlation value of plasma flow rate acquired by the plasma-flow-rate-acquiring unit;
wherein the colloid osmotic pressure (CP) is determined with a formula comprising: $CP=TMPa-TMPb$, wherein TMPa is a transmembrane pressure difference occurring when the liquid does not generate colloid osmotic pressure and TMPb is transmembrane pressure difference occurring when the patient's blood is supplied into the blood flow route with the filtration by an ultrafiltration pump.

14. A blood purification apparatus comprising:
a blood circuit including an arterial blood circuit and a venous blood circuit and that allows a patient's blood to extracorporeally circulate from a distal end of the arterial blood circuit to a distal end of the venous blood circuit;
a blood purifier provided between the arterial blood circuit and the venous blood circuit and that purifies the patient's blood flowing through the blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
an ultrafiltration unit that performs ultrafiltration by filtering out water from the patient's blood in the blood flow route through the blood purification membrane and draining the water through the dialysate flow route; and
a substitution-fluid supply unit that supplies substitution fluid into the blood circuit, and
a detecting unit that detects a transmembrane pressure difference occurring on the blood purification membrane under a pressure difference between liquid in the blood flow route and liquid in the dialysate flow route;

the blood purification apparatus comprising:
a colloid-osmotic-pressure-acquiring unit that acquires a colloid osmotic pressure of the patient's blood in the blood flow route or a correlation value of colloid osmotic pressure with reference to the transmembrane pressure difference occurring when liquid that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;
a plasma-total-protein-acquiring unit that acquires a plasma total protein or a correlation value of plasma total protein with reference to the colloid osmotic pressure or the correlation value of colloid osmotic pressure acquired by the colloid-osmotic-pressure-acquiring unit,
a plasma-flow-rate-acquiring unit that acquires a plasma flow rate or a correlation value of plasma flow rate with reference to a blood concentration detected from the patient's blood and the plasma total protein or the correlation value of the plasma total protein acquired by the plasma total protein acquiring unit; and
a control unit in communication with and controlling the colloid-osmotic-pressure-acquiring unit, the plasma-total-protein-acquiring unit, and the plasma-flow-rate-acquiring unit; wherein a substitution rate to be achieved by the substitution-fluid supply unit is calculated with reference to the plasma flow rate or the correlation value of plasma flow rate acquired by the plasma-flow-rate-acquiring unit;
wherein the substitution rate (Qs) is determined with a formula comprising: $Qs=Qpw*FF/100-Quf$ where Qpw is plasma flow rate, FF is a filtration fraction and Quf is an ultrafiltration flow rate.

15. A method of acquiring a plasma flow rate on a blood purification apparatus, the blood purification apparatus comprising:
extracorporeally circulating a patient's blood from a distal end of an arterial blood circuit to a distal end of a venous blood circuit of a blood circuit;
purifying the patient's blood through a blood purifier provided between the arterial blood circuit and the venous blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;
performing ultrafiltration with an ultrafiltration unit that filters out water from the patient's blood in the blood flow route through the blood purification membrane and draining the water through the dialysate flow route;
supplying substitution fluid with a substitution-fluid supply unit that supplies the substitution fluid into the blood circuit,
detecting, with a detecting unit, a transmembrane pressure difference occurring on the blood purification membrane under a pressure difference between liquid in the blood flow route and liquid in the dialysate flow route;
acquiring a colloid osmotic pressure of the patient's blood, with a colloid-osmotic-pressure-acquiring unit, in the blood flow route or a correlation value of colloid osmotic pressure with reference to the transmembrane pressure difference occurring when liquid in the blood flow route that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;

acquiring, with a plasma-total-protein-acquiring unit, a plasma total protein or a correlation value of plasma total protein with reference to the colloid osmotic pressure or the correlation value of colloid osmotic pressure acquired by the colloid-osmotic-pressure-acquiring unit;

acquiring, with a plasma-flow-rate-acquiring unit, the plasma flow rate or a correlation value of plasma flow rate with reference to a blood concentration detected from the patient's blood and the plasma total protein or the correlation value of the plasma total protein acquired by the plasma-total-protein-acquiring unit;

calculating, with reference to the plasma flow rate or the correlation value of plasma flow rate acquired by a plasma-flow-rate-acquiring unit, a substitution rate to be achieved by the substitution-fluid supply unit; and controlling the colloid-osmotic-pressure-acquiring unit, the plasma-total-protein-acquiring unit, and the plasma-flow-rate-acquiring unit with a control unit, wherein the colloid osmotic pressure (CP) is determined with a formula comprising: $CP=TMPa-TMPb$, wherein TMPa is a transmembrane pressure difference occurring when the liquid does not generate colloid osmotic pressure and TMPb is transmembrane pressure difference occurring when the patient's blood is supplied into the blood flow route with the filtration by an ultrafiltration pump.

16. A method of acquiring a plasma flow rate on a blood purification apparatus, the blood purification apparatus comprising:

extracorporeally circulating a patient's blood from a distal end of an arterial blood circuit to a distal end of a venous blood circuit of a blood circuit;

purifying the patient's blood through a blood purifier provided between the arterial blood circuit and the venous blood circuit, the blood purifier having a blood flow route through which the patient's blood extracorporeally circulating through the blood circuit flows and a dialysate flow route through which dialysate flows, the blood flow route and the dialysate flow route being separated from each other by a blood purification membrane for purifying the patient's blood;

performing ultrafiltration with an ultrafiltration unit that filters out water from the patient's blood in the blood flow route through the blood purification membrane and draining the water through the dialysate flow route;

supplying substitution fluid with a substitution-fluid supply unit that supplies the substitution fluid into the blood circuit, detecting, with a detecting unit, a transmembrane pressure difference occurring on the blood purification membrane under a pressure difference between liquid in the blood flow route and liquid in the dialysate flow route;

acquiring a colloid osmotic pressure of the patient's blood, with a colloid-osmotic-pressure-acquiring unit, in the blood flow route or a correlation value of colloid osmotic pressure with reference to the transmembrane pressure difference occurring when liquid in the blood flow route that does not generate colloid osmotic pressure is supplied into the blood flow route with filtration by the ultrafiltration unit withheld and the transmembrane pressure difference occurring when the patient's blood is supplied into the blood flow route with the filtration by the ultrafiltration unit withheld;

acquiring, with a plasma-total-protein-acquiring unit, a plasma total protein or a correlation value of plasma total protein with reference to the colloid osmotic pressure or the correlation value of colloid osmotic pressure acquired by the colloid-osmotic-pressure-acquiring unit;

acquiring, with a plasma-flow-rate-acquiring unit, the plasma flow rate or a correlation value of plasma flow rate with reference to a blood concentration detected from the patient's blood and the plasma total protein or the correlation value of the plasma total protein acquired by the plasma-total-protein-acquiring unit;

calculating, with reference to the plasma flow rate or the correlation value of plasma flow rate acquired by a plasma-flow-rate-acquiring unit, a substitution rate to be achieved by the substitution-fluid supply unit; and controlling the colloid-osmotic-pressure-acquiring unit, the plasma-total-protein-acquiring unit, and the plasma-flow-rate-acquiring unit with a control unit, wherein the substitution rate (Qs) is determined with a formula comprising: $Qs=Qpw*FF/100-Quf$ where Qpw is plasma flow rate, FF is a filtration fraction and Quf is an ultrafiltration flow rate.

* * * * *